(12) United States Patent
Walsh

(10) Patent No.: US 6,824,052 B2
(45) Date of Patent: Nov. 30, 2004

(54) HEALTHCARE VERIFICATION METHODS, APPARATUS AND SYSTEMS

(76) Inventor: Christopher S. Walsh, 303 Falling Creek Rd., Fredericksburg, VA (US) 22401

( * ) Notice: Subject to any disclaimer, the term of this patent is extended or adjusted under 35 U.S.C. 154(b) by 0 days.

(21) Appl. No.: 10/290,288

(22) Filed: Nov. 8, 2002

(65) Prior Publication Data

US 2003/0074228 A1 Apr. 17, 2003

Related U.S. Application Data

(63) Continuation-in-part of application No. 09/833,785, filed on Apr. 13, 2001, now Pat. No. 6,464,136, which is a continuation-in-part of application No. 09/473,138, filed on Dec. 28, 1999, now Pat. No. 6,497,358.

(51) Int. Cl.[7] .............................................. G06K 5/00
(52) U.S. Cl. .................. 235/380; 235/385; 235/379; 235/383; 235/382; 705/64; 705/65; 705/67; 705/75; 705/3
(58) Field of Search ................................ 235/380, 385, 235/379, 383, 382; 705/64, 65, 67, 75, 3

(56) References Cited

U.S. PATENT DOCUMENTS 6,342,839 B1 * 1/2002 Curkendall et al. ...... 340/573.3
6,347,329 B1 * 2/2002 Evans ......................... 709/202
6,366,651 B1 * 4/2002 Griffith et al. ............ 379/88.14
6,464,136 B2 * 10/2002 Walsh .......................... 235/380
6,497,358 B1 * 12/2002 Walsh .......................... 235/380
6,592,517 B2 * 7/2003 Pratt et al. .................... 600/300
6,597,948 B1 * 7/2003 Rockwell et al. ............... 607/5
6,603,464 B1 * 8/2003 Rabin .......................... 345/179

* cited by examiner

Primary Examiner—Thien M. Le
Assistant Examiner—Allyson N Trail
(74) Attorney, Agent, or Firm—Strites & Harbison PLLC; Ross F. Hunt, Jr.

(57) ABSTRACT

Methods, systems and apparatus are provided for, inter alia, verification of the identity of a patient undergoing healthcare administered by a healthcare practitioner. The methods include improved record and verify methods which provide for verification of healthcare data entered into a computer and for the use of a paper verification sheet or log into which selected data from the computer is entered. Methods are also provided which incorporate timing out of preselected periods to ensure that healthcare-related tasks or actions, including, e.g., those involving patient identification, are carried out promptly. In addition, improved check sheets or logs are provided which are specifically limited in the number of healthcare parameters to be monitored. Further, an improved document carrier is provided which helps ensure that the proper documents, arranged in a desired sequence, are brought to the treatment setting.

64 Claims, 16 Drawing Sheets

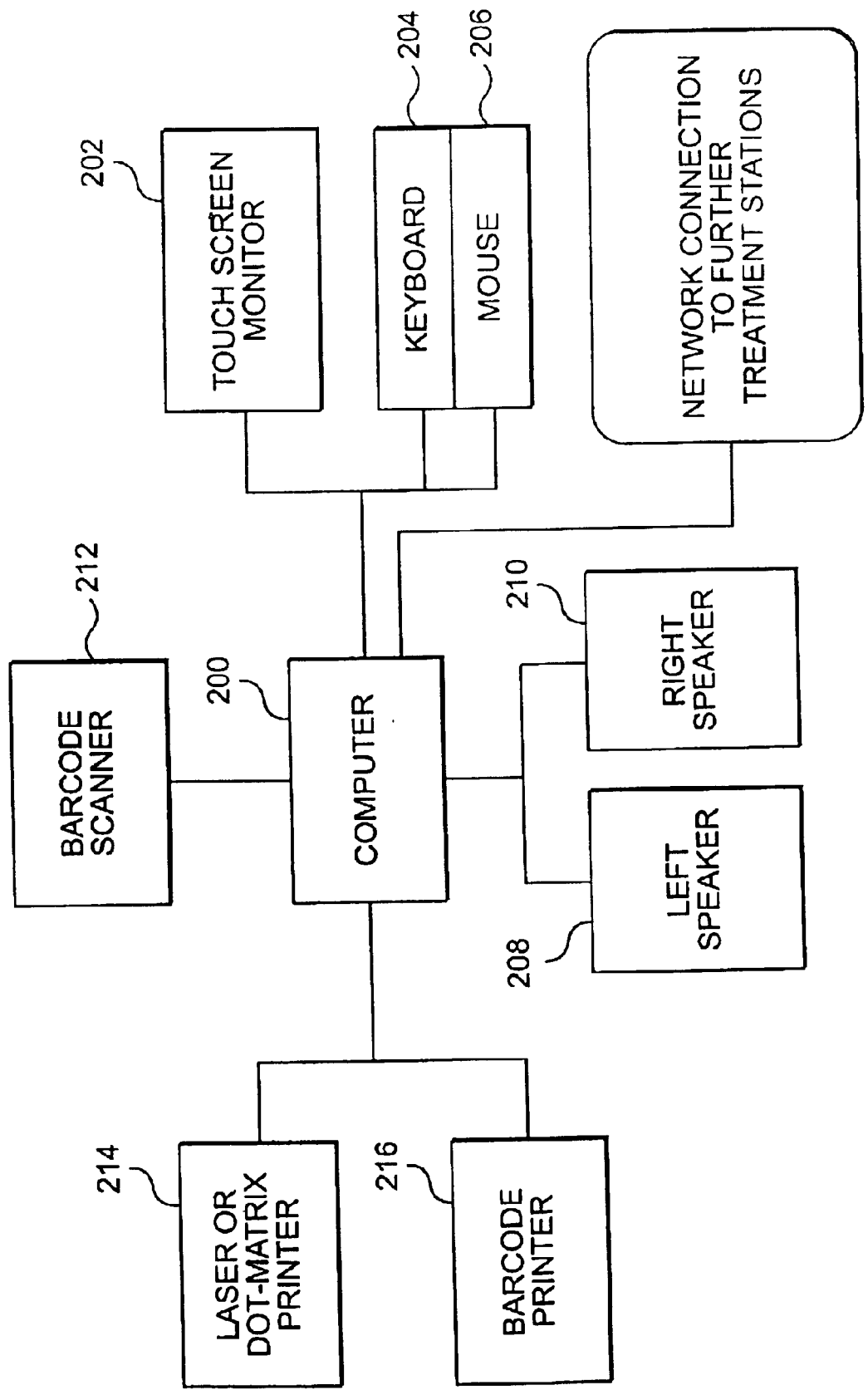

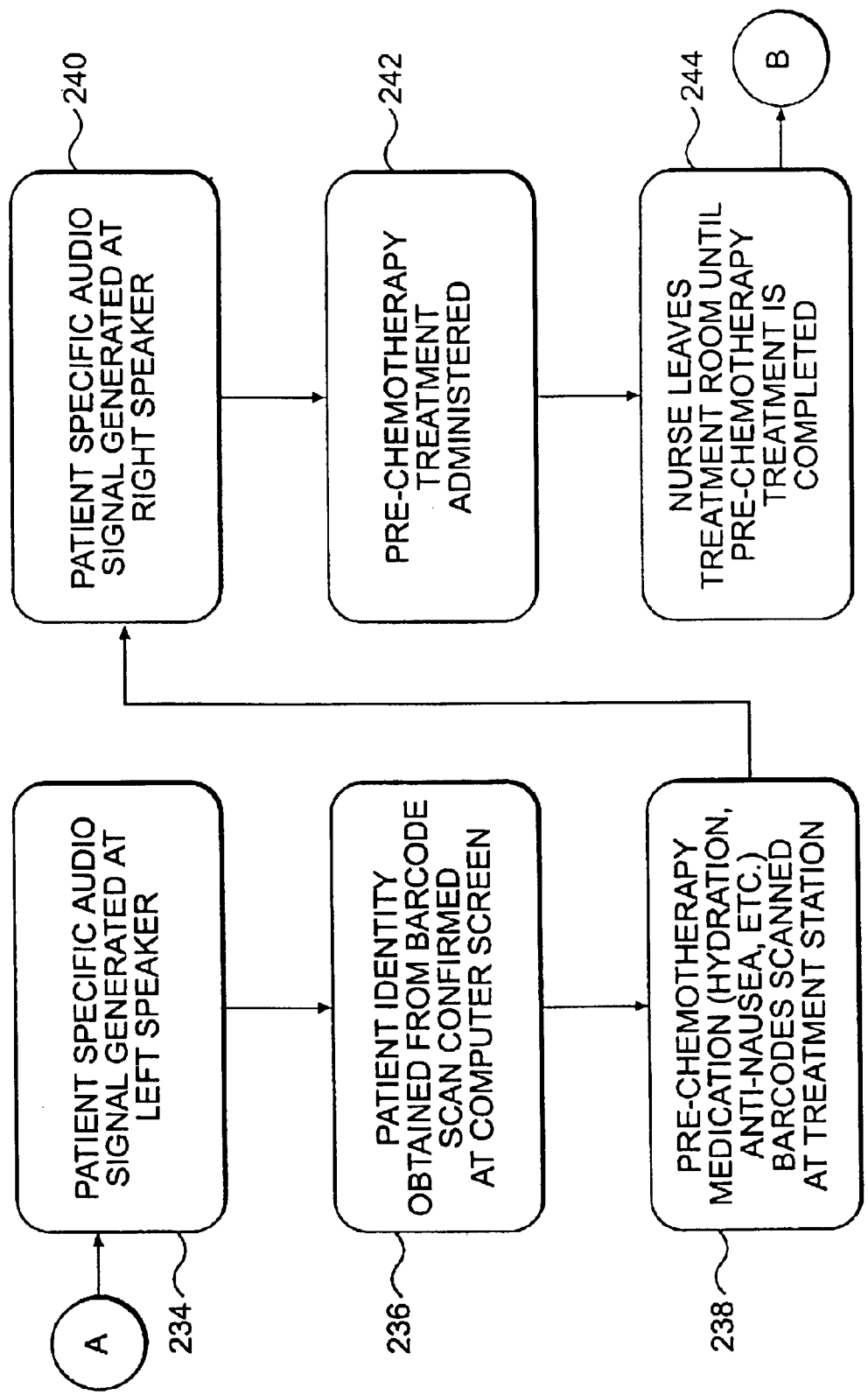

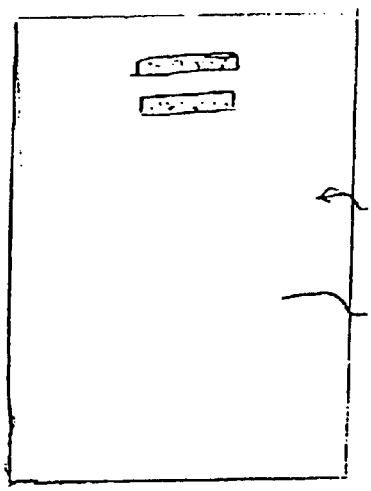
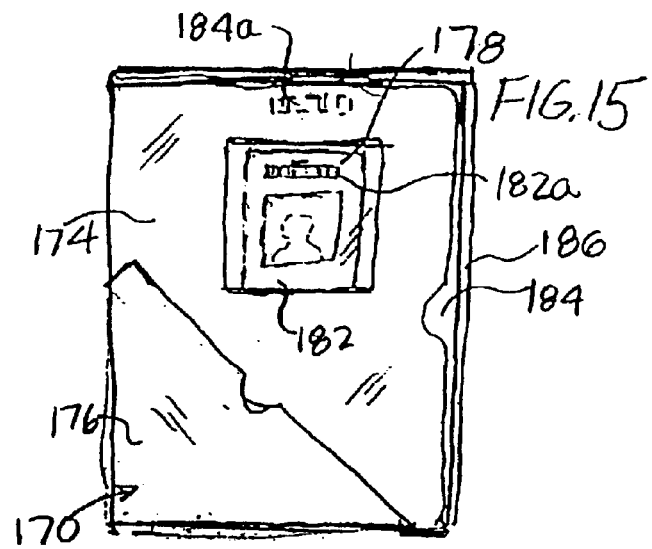
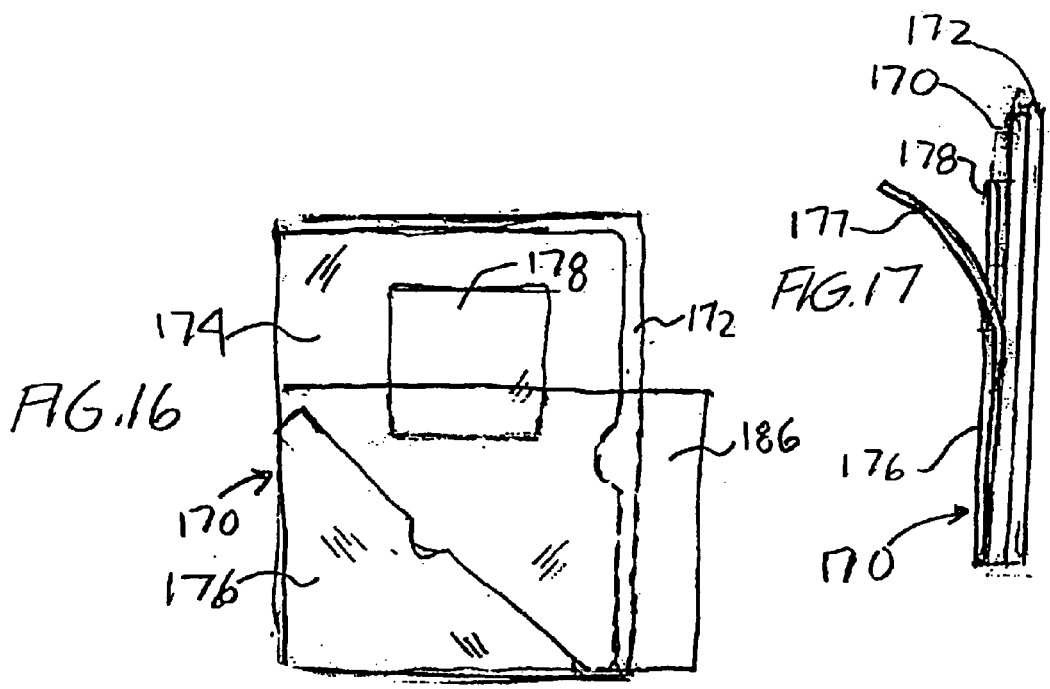

HEALTHCARE VERIFICATION METHODS, APPARATUS AND SYSTEMS

CROSS-REFERENCE TO RELATED APPLICATIONS

This application is a Continuation-In-Part of U.S. application Ser. No. 09/833,785, filed on Apr. 13, 2001, now U.S. Pat. No. 6,646,136, which is itself a Continuation-In-Part of Application Ser. No. 09/473,138 filed on Dec. 28, 1999, now U.S. Pat. No. 6,497,358.

FIELD OF THE INVENTION

The present invention relates to record and verify systems used in medical and other healthcare settings, and, more particularly, to improved record and verification systems and methods for such use which include a number of important features and advantages as compared with prior art systems and methods, including those currently in use.

BACKGROUND OF THE INVENTION

By way of background, it is instructive to briefly consider the history of verify and record systems used in connection with radiation therapy treatment of patients using linear accelerators or other megavoltage radiation units. Verify and record systems were originally designed to verify that radiation treatments were set up correctly by the radiation therapy technologist (RTT). This was accomplished through verification that certain key parameters were within predetermined tolerances. The verify and record process has evolved more recently into an automated set-up procedure that emphasizes rapid through-put, while de-emphasizing verification of treatment parameters that previously were set manually by the RTT. Some record and verify systems currently in use actually take control of the manual process by changing physician-selected field sizes, even though the field sizes fall within selected tolerance limits. The trend toward automated systems has led to reduced interaction between the user and the accelerator which has both positive and negative implications. The philosophy of delivering radiation treatment based on an automated set-up model is grounded in the desire to reduce the potential for human error in the set-up process. The downside of the automated or "black box" approach is the disengagement of the RTT from parameter adjustment, i.e., in relieving the RTT of the task of setting the patient treatment parameters through adjustment of the linear accelerator. The negative aspect of this is that if the RTT does not have to set the parameters manually, the RTT is less conditioned to perform the function manually and, therefore, less conditioned to detect errors when these errors occur, whether these errors are dosimetry programming or process errors and whether these errors occur in manual or automated set-up modes. When the RTT is detached from the procedure of manually setting up the patient for treatment, it becomes more difficult for the overall treatment process to recover should the automated process fail. In this regard, when an RTT sets up a patient manually, the RTT "rehearses" the recovery procedure that would be used if the automated primary process should fail. However, when automated set-ups are employed, the RTT is less "rehearsed" in recovering efficiently when the automated process is not available, because such rehearsal of recovery procedures is not integral to automated treatment delivery. The more safety critical the task, the more the recovery should be rehearsed.

Given current trends in the medical industry, the trend toward automated set-up is irreversible. Further, because of a number of factors including cost pressures, the trend toward staffing reduction is irreversible, at least in the near term. It also appears clear that the electronic record will not totally replace the paper chart, at least not in the near term. In this regard, even if it were proven better for patient care to chart electronically, physician resistance will hinder widespread adoption in the foreseeable future. In general, physicians will not abandon paper charts, either from habit or for medical-legal reasons. Accordingly, the need for maintaining a paper record during implementation of electronic medical record keeping will continue. As a consequence, a further vulnerability of automated radiation treatment systems (in addition to the disengagement of the RTT from the manual recovery process when the automated system is temporarily down), is the potential for mismatches between the electronic record and the paper medical record. These mismatches are commonly due to a failure of the RTT to document treatments in the paper record when the automated system logs the event. The problem of electronic record and paper mismatches is increasing in the specialty of radiation oncology, as reported by clinical medical physicists.

It should be understood that disengagement of the RTT from the manual recovery process increases risk for patient care because the verify and record systems, in many recent configurations, do not check for human error. Record and verify systems, when programmed and executed correctly, can prevent some errors, but not all. Record and verify systems in current use cannot detect human errors when the system itself is the primary process. Additionally, as indicated above, the disengagement of the RTT from linear accelerator parameter adjustment also can disengage the RTT from subtle cues regarding patient identification and radiation field placement. It would be desirable if record and verify systems were configurable to allow automated set-ups at selected times for certain radiation therapy technologists and not for others, such as, for example, when the manual skills of selected RTTs are being assessed. However, the overall trend is clearly toward automated set-up because of the improved throughput which results, as well as the industry-wide momentum toward multi-leaf collimator therapy, which is more optimally performed with automation.

Greater automated throughput can lead to greater risk for other reasons as well. Increased automation means greater potential for a mistake occurring through dose calculation error, with the danger of the error being repeated without prompt detection once the error does occur. The emphasis on throughput also increases the probability of errors in the actual treatment process, characterized by patient identification errors, field sequence errors and field alignment errors. Major preventable ways to harm patients through treatment process failures include (1) treating the wrong patient, i.e., treating a patient with a radiation treatment intended for another patient; (2) treating the right patient, but on a day when the patient is not supposed to receive treatment until other evaluations are performed first (e.g., treating a patient when the patient should have been seen by the doctor prior to the treatment delivery), and (3) treating the right patient but with the improper treatment set-up, i.e., treating with a wedged field without a wedge, treating with the wrong monitor units (MU) programmed into the accelerator, or treating with the wrong energy. In addition, as described above, in the event that the record and verify device should be temporarily unavailable due to a network, or other, problem, there is a distinct possibility or even an increased probability of parameter selection errors due to human error, because the process of automation can change the behavior of the user, making the user more dependent on automation. It is noted that more combination chemotherapy with radiation increases toxicity and therefore increases the potential harm that may occur to a patient if the patient receives the wrong treatment or if the patient is treated without proper evaluation before treatment. Moreover, pushing patients to the limit of tissue tolerance increases the potential for adverse events. Automated treatment may increase the possibility of undetected mistakes related to automated set-up, thereby increasing the possibility of patient injury.

As indicated above, the transition to automated treatment system tends to distract the RTTs for a number of reasons. First, and very basically, the new technology creates a new process. Further, the new process diverts RTTs from traditional cross checks in the treatment room. This is true of systems now in use such as the VARIS, IMPAC and LANTIS systems. In addition, visual distractions are created and the RTTs are diverted from paper chart documentation which can be critical in the safe treatment of a patient.

Although the focus above has been on radiation therapy, it will be appreciated that similar problems exist in other medical treatment and healthcare settings including chemotherapy as well as in neonatal care, dispensing of medications on both an inpatient and outpatient basis, nursing care and other healthcare in nursing homes, and in other inpatient and outpatient applications wherein patient verification, medication verification, medication delivery device verification, healthcare delivery verification and the like are of importance.

SUMMARY OF THE INVENTION

According to the invention, methods, devices and systems are provided which ameliorate or overcome a number of important problems associated with methods and systems currently in use as is discussed in more detail below.

In accordance with one aspect of the invention, there is provided a record and verify method for use in monitoring healthcare administered to a patient, the method comprising the steps of:

(a) initially entering, into a computer monitor, data corresponding to the healthcare to be administered;

(b) verifying the patient healthcare data entered into the computer monitor against at least one source;

(c) entering data from the computer monitor into a paper verification sheet;

(d) administering the healthcare to the patient; and (e) updating a patient record after the healthcare has been administered.

Preferably, the step of updating a patient record comprises making an entry into the computer that the healthcare has been administered.

Advantageously, the method further comprises checking and signing the paper verification sheet. The step of updating a patient record preferably comprises making an entry into the computer that the healthcare has been administered and the step of checking and verifying the paper verification sheet is carried out after said entry.

In one preferred implementation, the data corresponding to the healthcare to be administered that is entered into the computer monitor is previously stored and is automatically downloaded into the computer monitor at the request of an operator.

In another preferred implementation, the data corresponding to the healthcare to be administered is entered into the computer monitor from a patient healthcare administration chart.

In one preferred embodiment, the method is used with a radiation therapy treatment system including a radiation treatment device for providing radiation treatment and the computer monitor comprises a radiation treatment monitor and an associated computer for monitoring the radiation treatment device. Further, the healthcare data comprises radiation treatment data and the radiation treatment data is entered into the treatment monitor from a patient treatment chart and the step of administering healthcare comprises using the radiation treatment device in treatment of the patient. The step of using the radiation treatment device generates actual treatment data, and the step of updating a patient record preferably comprises entering said actual treatment data into the patient treatment chart, and the method preferably comprises the further step of: (f) checking and signing (e.g., by initialing and dating) the data entered into the patient treatment chart and into the paper verification sheet.

In one preferred implementation of this embodiment, first and second radiation therapists carry out the method, and the first therapist is responsible for at least step (e), the second therapist is responsible for at least steps (b) and (c) and both therapists carry out, and are responsible for, step (f). Preferably, after treatment data is entered into the treatment monitor and the data entered is displayed on a monitor screen associated with the treatment monitor, the first therapist recites aloud selected treatment data from the patient treatment chart and the second therapist verifies the recited treatment data against the data entered into treatment monitor as displayed on said monitor screen. Advantageously, the second therapist verbally recites the treatment data displayed on said monitor screen. Preferably, both the first and second therapists initially view, on a monitor screen associated with the treatment monitor, treatment data entered into the treatment monitor, the first therapist then recites aloud selected treatment data from the monitor screen, the second therapist, while still viewing the monitor screen, verifies the selected treatment data, in real time, as recited by the first therapist, the second therapist, while still viewing the monitor, recites aloud the preselected treatment data from the monitor screen, the first therapist, when still viewing the monitor screen, verifies the preselected treatment data, in real time, as recited by the second therapist, and the second therapist then enters the preselected treatment data into the paper verification sheet.

In a further preferred implementation of this embodiment, only selected treatment data, of the patient treatment data that is entered into the treatment monitor, is entered into the paper verification sheet. Advantageously, the selected treatment data consists of the (i) presence or absence of a wedge, (ii) the energy level used, and (iii) the monitor units used.

In another preferred implementation of this embodiment, wherein multiple radiation fields are delivered to the patient, steps (a) to (e) above are repeated for each field, and the method further comprises entering of a cumulative radiation dose into the patient treatment chart when all of the multiple treatment fields have been delivered.

In accordance with a further aspect of the invention there is provided a method for use in carrying out a medical treatment wherein a computer and a computer monitor including a monitor screen are used at least in setting up of the medical treatment, the method comprising:

setting a time period in which at least one action requiring interfacing with the monitor must be carried out;

monitoring whether the at least one action has been carried out during said time period; and if the at least one action is not carried out within said time period, at least temporarily providing that the medical treatment is not to proceed.

In a first preferred implementation, the step of at least temporarily providing that the medical treatment is not to proceed comprises providing that the at least one action must be carried out within a new time period before the medical treatment can proceed.

In another preferred implementation, the step of at least temporarily providing that the medical treatment is not to proceed comprises blanking out the monitoring screen.

In yet another preferred implementation, the step of at least temporarily providing that the medical treatment is not to proceed comprises providing a prompt on the monitor screen which requires a predetermined reply before the medical treatment is to proceed.

In one preferred embodiment of the first implementation, the at least one action comprises at least two separate actions, each with a separate time period for completion. In another embodiment, the at least one action comprises at least two actions both of which must be completed within said period. In an embodiment wherein the medical treatment includes the use of a treatment unit controlled by the computer and monitor, the step of at least temporarily providing that the medical treatment is not to proceed if the at least one action is not completed during said time period comprises prohibiting use of the treatment unit. Advantageously, use of the treatment unit is prohibited by disabling the monitor.

Preferably, the at least one action comprises (i) scanning of an identifier member, including a patient identifier, using an optical scanner associated with the computer monitor, and (ii) scanning of a patient treatment sheet, including said patient identifier, using said optical scanner, and use of said treatment unit is prohibited if either said scanning is not carried out during said time period. In an advantageous implementation, a characteristic audio signal, previously assigned to the patient undergoing the medical treatment and unique to the patient, is generated for each said scanning wherein the patient identifier matches an identifier for the patient stored by said computer. Preferably, when each said scanning is successfully completed, a further predetermined time period is started for use of said treatment unit, and use of said treatment unit is prohibited at the end of said further period. Advantageously, after use of said unit is prohibited, the computer monitor displays a query on the monitor screen as to whether treatment is continuing and, in response to entry of a positive reply, enables the treatment unit. Preferably, when use of said unit is prohibited, the monitor displays on the monitor screen a query requesting confirmation that the patient treatment sheet has been updated. In one important embodiment, the at least one action further comprises scanning of an identifier by at least one treatment practitioner within a predetermined time period prior to said scanning of the identifier member and the patient treatment sheet.

In a preferred embodiment of each implementation, the at least one action comprises scanning of an identifier by an optical reader associated with said computer monitor. In one specific embodiment, the identifier is carried by a medical instrument. In an advantageous implementation, the medical treatment comprises delivery of a drug and the medical instrument is a syringe. In another specific embodiment, the identifier comprises a patient photograph. In yet another embodiment, the identifier is associated with identifying member for one of (i) a patient undergoing the medical procedure and (ii) at least one treatment practitioner.

In all implementations of the method in accordance with this aspect of the invention, the at least one action preferably comprises providing identification of one of (i) a patient to be treated and (ii) at least one treatment practitioner, and the identification is provided by reading of an identifier by an optical reader associated with said control monitor.

In accordance with yet another aspect of the invention, there is provided a method for use in carrying out a medical procedure, using a treatment unit and a computer and monitor for controlling the treatment unit, so as to ensure that at least one action, requiring interfacing with the monitor, is completed in a timely manner, said method comprising:

initiating at the monitor, a start time for the at least one action to be carried out;

determining whether the at least one action has been carried out within a predetermined time period after said start time; and at least temporarily preventing access to the treatment unit if the at least one action has not been carried out within said predetermined period.

According to still another aspect of the invention, a check sheet is provided for use in administration of patient healthcare, the check sheet containing (i) entry spaces for entry by a healthcare caregiver of healthcare parameters for verification, and (ii) headings for the entry spaces each identifying a corresponding healthcare parameter, said healthcare parameters consisting of no more than three parameters excluding parameters relating to the time of administration of the healthcare.

Preferably, the check sheet further includes a heading for the time of day at which the patient healthcare is administered.

In one important implementation, the check sheet comprises a treatment check sheet for a patient undergoing radiation treatments, the treatment check sheet listing a plurality of treatment parameters for entry of data for verification by at least one radiation treatment practitioner prior to administration of a radiation treatment, said treatment parameters consisting solely of three patient specific parameters. Preferably, the three parameters consist of wedge presence, radiation energy level and monitor units. Advantageously, the treatment check sheet includes four rows or columns thereon, said rows or columns including headings and, following each of said headings, a plurality of empty spaces for entries by the treatment practitioner, said headings including wording indicating that the corresponding column is designated for entries with respect (i) the current date, (ii) the radiation energy level, (iii) the presence or absence of a wedge and (iv) monitor units. Preferably, the treatment check sheet includes at least one place thereon designated for checking off by a treatment practitioner using the treatment check sheet.

In accordance with yet another aspect of the invention, there is provided a method of assisting in full completion of a medical procedure for an individual patient undergoing the medical procedure, the method comprising:

assigning an audio signal to a patient and ensuring that the patient recognizes the assigned audio signal when said audio signal is generated;

generating said audio signal at a treatment site during the medical procedure so that the signal is heard by the patient;

providing for terminating of the audio signal only after treating personnel performs at least preselected action necessary to properly conclude the medical procedure; and instructing the patient to remain at the treatment site until the audio signal is terminated.

Preferably, the audio signal comprises a piece of music, the piece of music is played while the patient is on a treatment table, and the at least one action comprises updating of a treatment record for the patient.

According to a further aspect of the invention, there is provided a record and verify method for use with a radiation therapy system including a radiation treatment device for providing radiation treatment and a treatment monitor, including a computer, for monitoring the treatment provided by the radiation treatment device, the method comprising the steps of:

initially entering, into the treatment monitor, patient treatment data corresponding to that contained in a patient treatment chart;
  verifying patient treatment data entered into the treatment monitor against at least one source;
  entering treatment data from the treatment monitor into a paper verification sheet;
  cross checking the treatment data entered into said paper verification sheet;
  using the radiation treatment device in treating of the patient; and
  updating the patient treatment chart after said treating of the patient.

In accordance with yet another aspect of the invention, there is provided a record and verify method in monitoring the administration of a patient care intervention, the method comprising the steps of:

initially entering, into a computer including an associated monitor screen, data corresponding to the patient care intervention that is to be administered to a patient;
  accessing the computer by presenting to an optical detector associated with the computer an identifier corresponding to an identifier stored by the computer so that when there is a match between the presented identifier and the stored identifier, at least some of said entered data is displayed;
  administering a patient care intervention to the patient corresponding to the entered data displayed on the monitor screen;
  entering into a paper verification sheet selected data related to the patient care intervention administered to the patient; and
  making an entry into the computer that the patient care intervention has been administered.

According to a further aspect of the invention, there is provided a record and verify method for use in monitoring a medical treatment administered to a patient, the method comprising the steps of:

initially entering patient treatment data corresponding to that contained in a patient treatment chart into a computer including an associated monitor screen;
  verifying patient treatment data entered into the computer and appearing on the monitor screen against at least one source;
  entering selected treatment data from that appearing on the monitor screen of the treatment monitor into a paper verification sheet;
  cross checking the treatment data entered into the paper verification sheet;
  carrying out the treatment; and
  entering into the patient treatment chart (i) an indication that the treatment has been carried out and (ii) an indication of any differences between the treatment data entered into the paper verification sheet and any actual treatment data.

Preferably, the computer includes an associated optical detector and access to the computer is effected by presenting to the optical detector an identifier member carrying an identifier matching an identifier stored by the computer.

According to still another aspect of the invention, there is provided a record and verify method for monitoring a patient care intervention administered to a patient, said method comprising the steps of:

entering critical data received relating to a patient care intervention, along with the name of the patient and the time and date, into a pre-prepared paper log sheet;
  verifying the critical data entered with at least one source;
  carrying out the patient care intervention;
  entering data relating to the patient care intervention into a computer monitor; and
  checking off on the paper log sheet that the data has been entered into the computer monitor.

Preferably, if the patient care intervention is not carried out or is not fully carried out, the method further comprises marking the log sheet to indicate this.

In accordance with still another aspect of the invention, there is provided a document carrier for healthcare documents, the document carrier comprising:

a first, backing member;
  a second, transparent member affixed to said backing member so as to form a first pocket for the receipt of healthcare documents; and
  a third, transparent member affixed to the second member and forming a second, partial pocket for temporary receipt of at least one healthcare document normally received in said first pocket, said second pocket being easier to access and providing less secure holding of documents than the first pocket.

Preferably, the document carrier further comprises a transparent pocket member affixed to said second member in an area thereof separate from the third member. Advantageously, the pocket member comprises front and back walls selectively secured together along facing edges thereof to form a pocket having an upper opening between said walls, the back wall being secured to the second member. In a preferred embodiment, the first pocket contains a log sheet and a guide sheet, the log sheet is disposed adjacent the second member and carries a machine readable, patient specific identifier which is machine readable through said second member and the pocket member contains a patient identification element carrying a machine readable, patient specific identifier which corresponds to the patient specific identifier carried by said log sheet and which is machine readable through said front wall of said pocket member.

In a preferred implementation, the third transparent member is triangular in shape and is attached at two side edges thereof to said second transparent member. Advantageously, the two side edges are affixed to said second member by heat sealing, the side edges comprise a lateral edge and a bottom side edge and the lateral edge has a length of at least 7 inches.

According to a further embodiment, there is provided a record and verify method for monitoring a caregiver intervention, the method comprising:

providing an electronic presentation of an inquiry as to whether a particular patient intervention administered by a caregiver is best characterized as full, partial or none;

prompting the caregiver to provide a simple response to the inquiry; and recording the response of the caregiver to the inquiry for future use.

Preferably, the inquiry is presented in a dialog box on touch sensitive computer screen and the caregiver responds by touching an appropriate screen location.

Further features and advantages of the present invention will be set forth in, or apparent from, the detailed description of preferred embodiments thereof which follows.

BRIEF DESCRIPTION OF THE DRAWINGS

FIG. 8 is a block diagram of a treatment station in accordance with yet another embodiment of the invention;

FIGS. 9(a) to 9(d) are, taken together, a block form flow chart of a chemotherapy treatment method in accordance with an additional embodiment of the invention;

FIGS. 12, 13 and 14 are a front elevational view, side elevational view and rear elevational view, respectively, of a healthcare document carrier in accordance with a preferred embodiment of a further aspect of the invention;

FIGS. 15 and 16 are front elevational views similar to FIG. 12 showing the document carrier in use; and FIG. 17 is a side elevational view similar to FIG. 13 used in explanation of an aspect of the construction of the document carrier.

DESCRIPTION OF THE PREFERRED EMBODIMENTS

Figure 1:
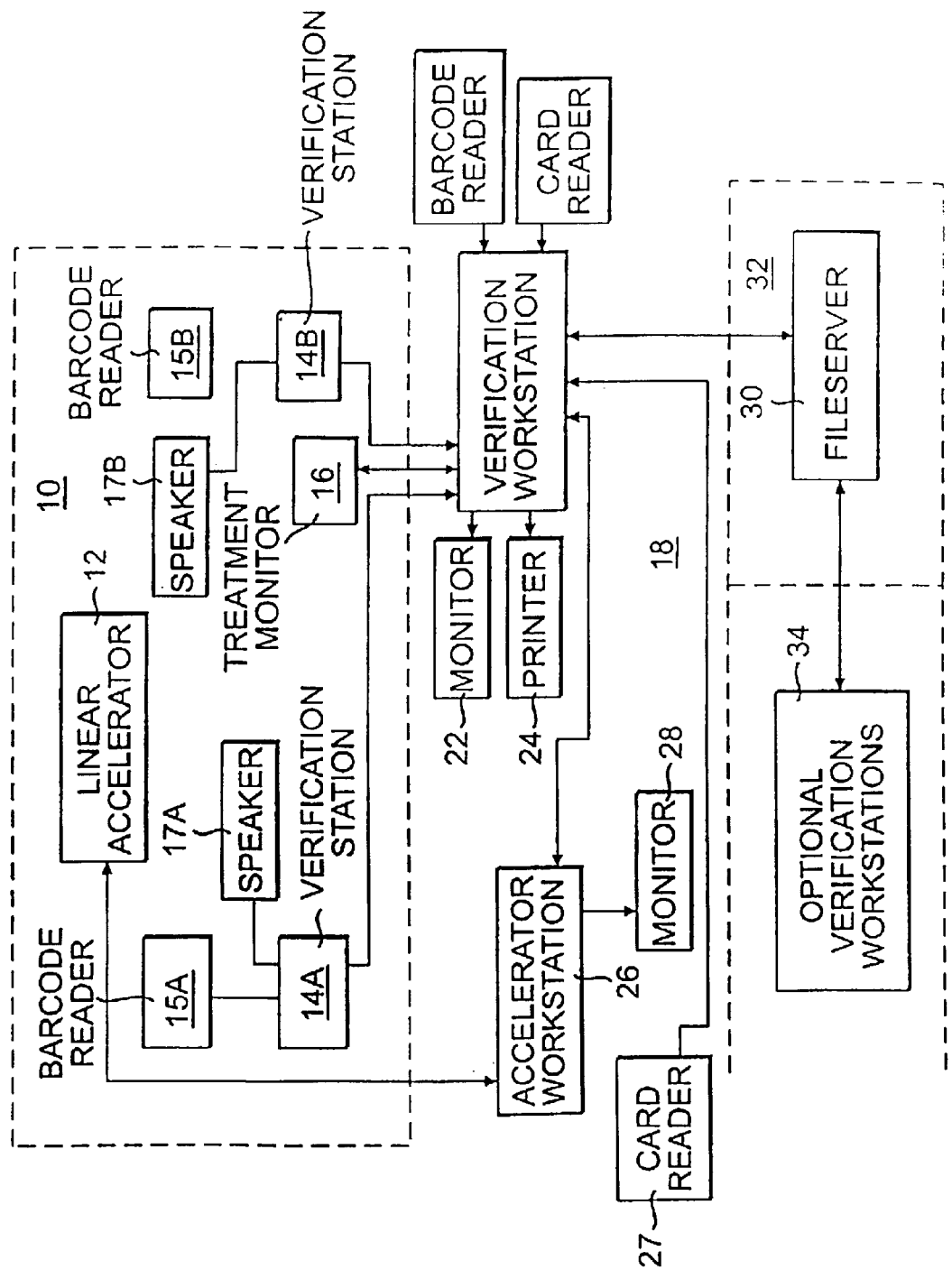
FIG. 1 is a block diagram of a record and verify system in accordance with one preferred embodiment of the invention.

Referring to FIG. 1, a block diagram is provided of one preferred embodiment of the overall system as applied to a radiation therapy setting. A treatment room 10 includes a conventional linear accelerator 12 which administers the radiation treatment to the patient and which may be any conventional analog or digital system. Two laser verification stations 14A and 14B are provided in the treatment room 10 along with a treatment monitor 16. The stations 14A and 14B are identical and each preferably includes a respective barcode reader 15A and 15B and a speaker 17A and 17B placed into a single mountable box (not shown). In a preferred embodiment, the verification stations 14A and 14B are located across the treatment room 10 from each other, just beyond the isocenter in the direction of the maze, with the linear accelerator 12 being located between the stations 14A and 14B. Further, the stations 14A and 14B should be situated so that a first technologist, Technologist A, is able to scan a chart or identification card or photograph (not shown) at station 14A on the wall (the left wall is viewed in FIG. 1) while a second technologist, Technologist B, is able to scan a patient's paper verification sheet (as referred to as an electronic sheet, or e-Sheet) at station 14B on the opposite (right) wall. As described below, the e-Sheet is a verification sheet used by the technologist during treatment which shows scheduled and actual treatments. With this setup, each technologist faces towards the gantry of the accelerator 10 and the patient. It is possible to scan the chart on the right rather than the left wall but the e Sheet would then have to be scanned on the left wall scanner. It is understood that while the terms "technologist" or "therapist" are used throughout, the actions described can be be carried out by any qualified person including qualified doctors, nurses and other hospital personnel and these terms are intended to cover this.

The treatment monitor 16 is used to display the name of the patient and the treatment field values, i.e., the actual fields which are used by the accelerator 10 and which are verified by the verification system. A typical listing of the treatment fields is provided in Table 1 below.

TABLE 1

Treatment Chart Fields and Descriptions

| Number | Description |
|---|---|
| 1 | Hospital Reference Number |
| 2 | Radiation Oncology Number |
| 3 | Protocol Number |
| 4 | Patient's Date of Birth |
| 5 | Referring Doctor's Name, Address, Phone Number and Identification number |
| 6 | Patient's Name |
| 7 | Patient's Address |
| 8 | Patient's Home Phone Number |
| 9 | Patient's Work Phone Number |
| 10 | Patient's Diagnosis |
| 11 | Diagnosis ICU-9 Code |
| 12 | Palliative or Radical |
| 13 | Definitive |
| 14 | Adjuvant |
| 15 | Pre-Op |
| 16 | Post-Op |
| 17 | Chemotherapy |
| 18 | Series Number |
| 19 | Current Date |
| 20 | Site to be treated |
| 21 | Field Description |
| 22 | Rx Dose |
| 23 | Dose per Fraction |
| 24 | Cumulative Dose |
| 25 | Number of Fractions |
| 26 | Energy |
| 27 | Modify |
| 28 | Reassess |
| 29 | Stop |
| 30 | Planned Rest |
| 31 | Total Treatments Planned |
| 32 | Physician Signature |
| 33 | Previous Radiation Technologist |
| 34 | Consent Signed |
| 35 | Collimator Size |
| 36 | SAD/SSD |
| 37 | Gantry Angle |
| 39 | Collimator Angle |
| 40 | Drum/Table Angle |
| 41 | Tray/Wedge |

TABLE 1-continued

Treatment Chart Fields and Descriptions

| Number | Description |
|---|---|
| 42 | Monitor Units |
| 43 | Comments |
| 44 | Port Film Verifications |
| 45 | Inpatient/Outpatient |
| 46 | Elapsed day count for number of treatments (can start at 0) |
| 47 | Radiation Treatment Technologist |
| 48 | Monitor Units |
| 49 | Tumor Dose Cumulative dosage |
| 50 | Physics |

Located outside of the treatment room in a treatment console area 18 is a verification workstation 20 including a verification monitor 22 (e.g., a standard twenty-one inch color monitor) and an associated high-speed printer 24 connected to the verification workstation 20. Also located in area 18 is an accelerator workstation 26 including a card swipe reader 27 and an accelerator monitor 28. The verification workstation 20 basically comprises a personal computer (e.g., NT 4.0) with a keyboard and mouse, which are not illustrated, together with a barcode reader which is shown separately at 21 and a mounted card swipe reader shown separately at 23. The workstation 20 preferably has a minimum of a 10-Megabyte hard drive and 64 Megabytes of memory.

As indicated in FIG. 1, the system also includes a fileserver 30 for the verification workstation 20 which is normally located in a secured room 32. Preferably, there is a TCP/IP connection from the verification station 20, and the file server 30 has enough memory to support at least one verification workstation. The system may also include further, optional verification workstations 34 for running an administration function described below.

For shorthand purposes, the method of the invention will be referred to hereinbelow as the VEEBAAT method or process, and the verification workstation 20 will also be referred to as the VEEBAAT workstation. Moreover, certain terminology will be used which is explained below and which, for the sake of convenience, is capitalized in the description which follows and also defined in the glossary set forth below.

Before consideration of the process in detail, it is noted that the VEEBAAT process may take various paths based on its configuration. For example, the configuration may be set up for each patient daily, or just once. The basic configurable parameters are Treatment Fields, technologist, patient and day of the week. Any combination of parameters may be configured. The VEEBAAT verification process may be run at the verification (VEEBAAT) workstation 20 in an Auto Setup Mode or Manual Setup Mode. The mode refers to how the Treatment Field Values are entered into the accelerometer (PRIMUS) workstation 26. A Manual Setup will have the Treatment Field Values manually entered at the accelerator workstation 26 and an Auto Setup will have the Field Values automatically downloaded from the VEEBAAT workstation 20 which electronically sends the treatment parameters automatically to the Accelerator workstation 26. The VEEBAAT process may be configured for Auto or Manual Setup based on four parameters: the technologist, the patient, the current day, and the treatment. The technologist parameter has highest priority, i.e., if a particular technologist is configured for VEEBAAT Manual only, then Manual will take precedence over Auto setup.

It is noted that the process is configured for two laser verification stations 14A and 14B in the treatment room 10 but may be overridden to operate with one of the laser verification stations if the other laser verification station fails.

Regarding the VEEBAAT workstation 20, the process is configured with the single, above-mentioned barcode reader 21 located at the VEEBAAT workstation 20 with the VEEBAAT Verification Function. The VEEBAAT workstation barcode reader 21 functions only to enable access to the application, not to perform the "echo function" (bar-coded photo/e-sheet cross check) described below.

The process is configured to display various reports at VEEBAAT startup. The reports are as follows: partial treatment report, cumulative dose reached report, and scheduled patient report. The reports will be displayed on monitor 22 in a scrolling fashion that can be controlled by the person viewing the reports. The partial treatment report will give a listing of patients who received partial treatment the previous day. This report will include the date and the patient's name. The cumulative dose reached report will list patients who have or will exceed their prescribed cumulative dose. The patient's cumulative doses is prescribed by the Radiation Oncologist. The report will include the date and the patient's name. The scheduled patient report will list all patients who are scheduled for treatment on that date. The report will include the patient's name and time of treatment.

Figure 2:
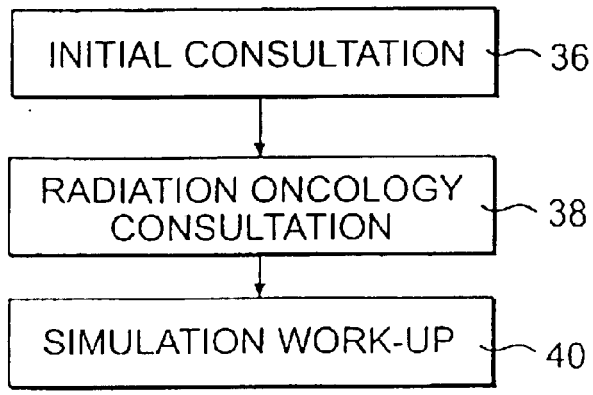
FIG. 2 is a flow chart of an initial consultation sequence involving the patient to be treated.

As an initial matter, referring to FIG. 2, a Patient's File is created on the patient's initial visit. A Patient's File creation consists of the initial consultation and, if advised, the patient's radiation oncology consultation. These steps are indicated in FIG. 2 by blocks 36 and 38. These particular sections of the Patient's File determine if a patient should be treated and, if so, the treatment strategy. A patient's initial consultation determines if radiation therapy is advisable. A radiation secretary creates a Red Folder. The folder contains the patient's referral and medical history. If treatment is advised, a patient is set up for a radiation oncology consultation. Otherwise, the patient's Red Folder will be archived. A radiation oncology consultation determines a patient's prescribed treatment. The patient's initial Red Folder is then moved to a White Folder. The patient's VEEBAAT account is created along with a Treatment Folder. The White Folder is a permanent folder for a patient. It will contain the initial Red Folder's contents and radiation oncology consultation.

After completion of a patient's scheduled treatments, all documents in the Treatment Folder are moved to the patient's White Folder. The Treatment Folder is used during the patient's treatments. The folder contains a Treatment Chart, e Sheet, patient set-up photographs and the patient's Polaroid Photo. These items are discussed below. The Treatment Folder also contains the dose calculation work sheets and simulation data, consent form and computer isodose plans, as well as in-vivo dosimetry data. The purpose of using two folders per patient is to reduce conflicts during treatment caused by situations in which radiation treatment technologist (R.T.T.) and nursing personnel simultaneously require access to the medical record. The White Folder and Treatment Folder are presented to the Radiation Oncologist for telephone calls, patient encounters, dictation, and the like. The Treatment Chart contains a patient's original prescription and treatment schedule signed by the Radiation Oncologist. The chart is used during treatment by the Technologist to manually enter Treatment Field Values into the accelerator workstation 26. Typical Treatment Field Values are set forth in Table 2 below.

TABLE 2

| Number | Name |
| --- | --- |
| 1 | Monitor Units |
| 2 | Jaw/Collimator Size |
| 3 | Collimator Angle |
| 4 | Gantry Angle |
| 5 | Table Drum Angle (optional) |

The e Sheet is, as mentioned above, used during the verification process to store prescribed and actual Treatment field Values. A new Treatment Folder will receive a blank e Sheet. A barcode is attached to the e Sheet. A detailed listing of fields and descriptions is provided above. Each Treatment Folder contains patient's set-up photographs to indicate the area for treatment along with tattoo markings. Each Treatment Folder also contains a patient's Polaroid Photo. This photograph or picture is used during the verification process to help insure the Treatment Folder belongs with the patient being treated. A barcode is attached to the Polaroid Photo.

The method and system of the invention lends itself well to accounting and billing tasks. As a first step, the patient's VEEBAAT Account is created. The account is used in the verification procedure during treatments. The account is generated on a VEEBAAT verification workstation 20 (or one of the optional workstations 34) using the VEEBAAT Administration Function. A typical chart with a detailed listing of fields and descriptions is provided in Table 3 below. Barcodes on the patient's e Sheet and Polaroid photo will be associated to the patient's VEEBAAT Account. As described in more detail below, the patient will be assigned a unique audio signal (e.g., a three tone audio signal in the exemplary embodiment under consideration) that will be used for audio verification by each of the patient, Technologist A and Technologist B in the Treatment Room prior to treatment.

TABLE 3

| Patient Information | |
| --- | --- |
| RT#: | |
| Patient Name: | |
| Date of Birth: | |
| Referring MD: | (link into UPIN chart) |
| City of Residence: | |
| Telephone No (home): | |
| Telephone No (work): | |
| Diagnosis: | {ascii text} |
| ICD 9 Code: | (link into ICD 9 chart) |
| Chemotherapy | y/n |
| Hormone Therapy | y/n |
| Bar code - Polaroid photo: | |
| Bar code - e Sheet: | |
| (link to actual treatment delivered) | |

A simulation system provides access to a comprehensive library of treatment strategies, including treatment protocols, simulation checklists, guides on how to order tests, and test rationale and, as indicated by block 40 in FIG. 2, a simulation work-up can be provided as part of the initial consultation process.

Turning now to the actual patient treatment process which is one key aspect of the present invention, and referring to FIGS. 3A to 3D, the patient arrives for treatment as indicated by block 42 and checks in with the receptionist. Technologist A obtains the patient's Treatment Folder, scans the patient's Polaroid Photo at the treatment console or workstation 20 to initiate VEEBAAT Verification Function, and ensures the patient matches the patient Polaroid Photo, as indicated by block 44. If there is a match, Technologists A and B escort the patient to treatment room 10 (block 46). Technologist B obtains the patient's e Sheet from the Treatment Folder. Technologist A scans the photo at the barcode reader 15A of the verification station 14 (block 48). If Technologist A is unable to scan the photo for any reason, a Supervisor will be requested to help resolve the problem. Once the photo has been successfully scanned, the VEEBAAT verification workstation 20 will associate the photo with the patient's VEEBAAT Account in the VEEBAAT Database (block 50). If the patient's VEEBAAT Account is not found, an Audio Error Signal ("beep") will be emitted and a Supervisor will be required to resolve the problem.

Considering in more detail the steps which take place, after Technologists A and B escort the patient into Treatment Room 10, the patient is correctly positioned on treatment table. Technologist A proceeds to either laser verification station 14A or 14B. Technologist B proceeds to other laser verification station. It will be assumed here that Technologist A is at station 14A and Technologist B is at station 14B. Technologist A then scans barcode on the patient's Polaroid Photo at the barcode reader 15A (block 48). The barcode is passed to the VEEBAAT Verification Function at the verification workstation 20 to ensure the barcode matches the Polaroid Photo bar code that was just scanned outside the treatment room at the verification workstation 20. If valid, the patient's audio signal is emitted at the verification station 14A. If the Technologist fails to scan the Patient's Polaroid Photo at the VEEBAAT verification workstation 20, an Audio Error Signal is issued. This will require the Technologist to go back to the VEEBAAT verification workstation 20 to scan the Patient's Polaroid Photo bar code to initiate the VEEBAAT Verification Function. Further, if the bar code scanned at barcode reader 15A of verification workstation 14A is a valid VEEBAAT account bar code, but does not match the bar code previously scanned at the VEEBAAT verification workstation 20, an audio Error Signal will be emitted in this case as well and a Supervisor will be required to resolve the problem. If the patient's e Sheet bar code is scanned first, i.e., if the bar code scanned is the e Sheet bar code associated with the current VEEBAAT Account, an audio Warning Signal is issued and the system waits for the Patient's Polaroid Photo bar code to be scanned. If the bar code is not a valid VEEBAAT bar code, it will be considered to be a read error. The VEEBAAT verification workstation will emit an audio Warning Signal and wait for a re-scan. Considering other potential failures, if the bar code is found but the patient cannot be treated, an audio Error Signal is issued. Again a Supervisor is required to resolve this problem. If the patient's cumulative dose exceeds or will exceed the patient's prescribed dose, a stop order is issued. In this regard, the patient's VEEBAAT Account has a stop treatment flag set, which is determined by the Radiation Oncologist.

The patient name and scheduled Treatment Field Values from the selected VEEBAAT Account are displayed on the treatment monitor 16 in a large font for easy readability. Also, if a port verification film (PVF) is scheduled, a reminder will appear on the treatment room monitor 16 to remind the technologists. Technologists A and B will visually verify that the name displayed on the monitor matches the patient's name. If not, a Supervisor shall be called to resolve the problem.

Figure 3A:
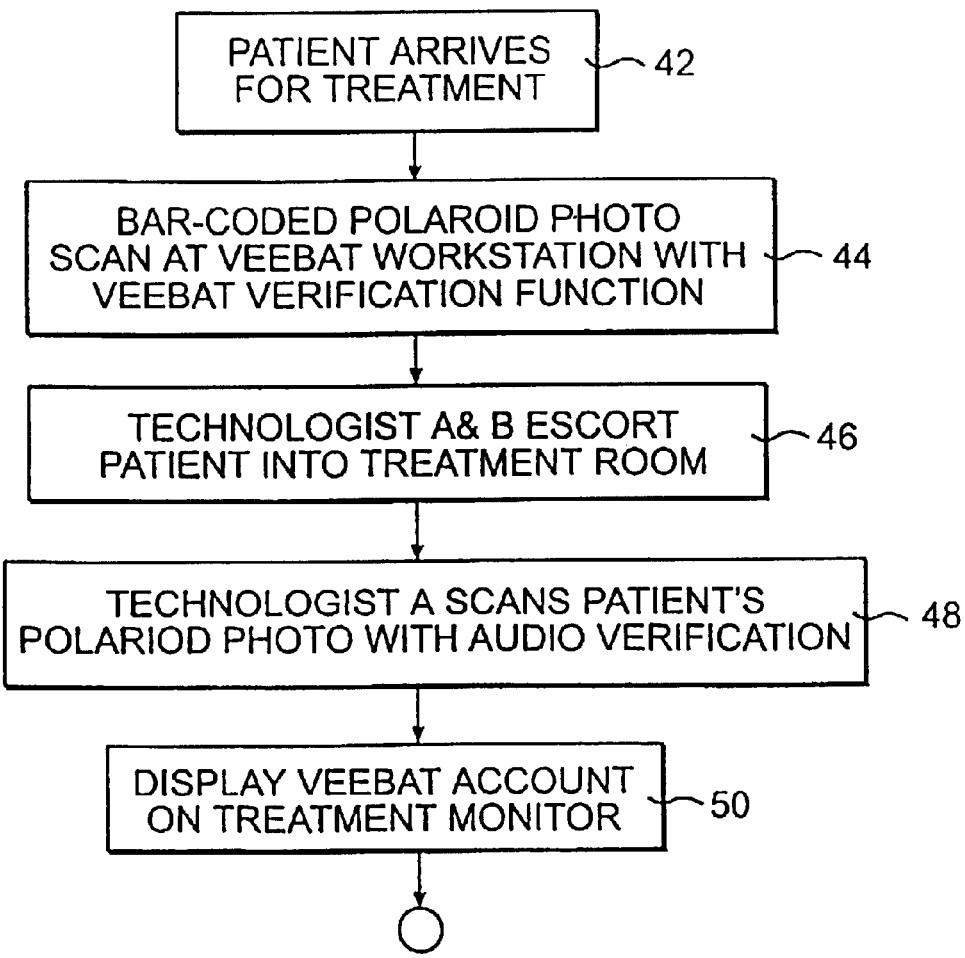
FIGS. 3A, 3B, 3C and 3D, taken together, are a flow chart of a record and verify method in accordance with one preferred embodiment of the invention.
Figure 3B:
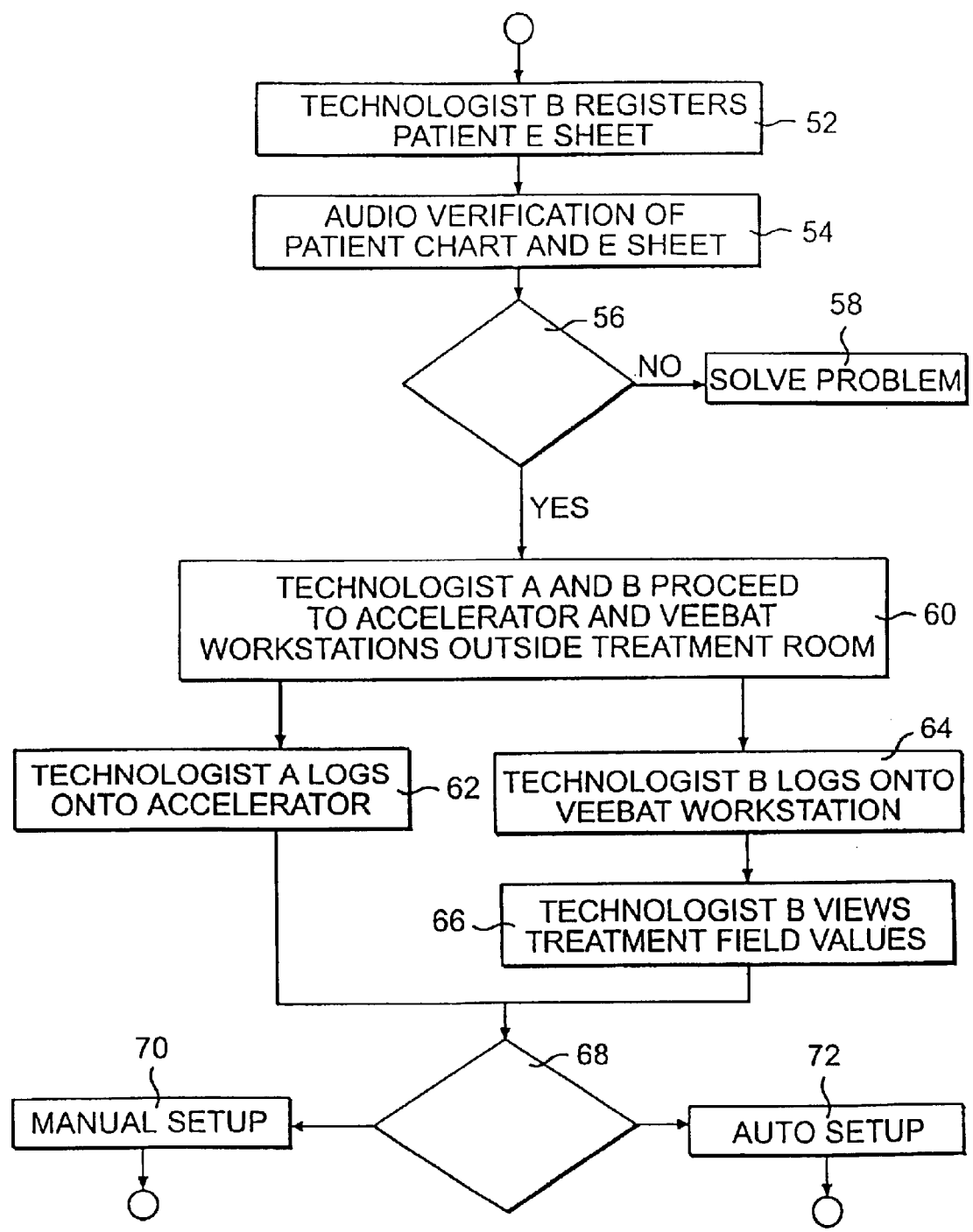

Referring to FIG. 3B, in the next step, Technologist B scans the patient's e Sheet bar code, as indicated by block 52 at barcode reader 15B of verification workstation 14B. The VEEBAAT Verification Function then verifies that the bar code is assigned to the patient's VEEBAAT Account. Verification of the patient chart and e Sheet is then provided. As shown by decision diamond 56, if valid, i.e., if there is a match, the patient's audio signal is emitted. If there is no match, an audio Error Signal is emitted and a Supervisor is required to resolve this problem (block 58). When the tone is emitted, Technologist A, Technologist B, and the patient all verify that the audio signals emitted from Verification Stations 14A and 14B are the same. The use of identification signals such as unique audio signals is an important aspect of the invention and, among other advantages, provides a comfort level for the patient that is not available with other methods and systems. If anyone questions the comparison of the audio signals, a Supervisor is required to resolve this issue. This aspect of the invention, i.e., the use of an audio signal unique to the patient and the requirement that the patient and the technologist (or technologists) in attendance all verify the signal, is discussed in more detail below.

Next, as shown by block 60, Technologist A proceeds to accelerator workstation 26 and Technologist B proceeds to the VEEBAAT verification workstation 20 to access the VEEBAAT Verification Function. Technologist A logs onto the accelerator workstation 26 (block 62) and uses the card swipe reader 27 located on the accelerator workstation 26 to register with the Verification Function of the VEEBAAT verification workstation 20. If Technologist A is unknown or does not have privilege to apply treatment, then the Verification Function of the verification (VEEBAAT) workstation 20 will display a message at the VEEBAAT workstation indicating the discrepancy. A Supervisor will be required to resolve this problem.

Technologist B logs onto the VEEBAAT verification workstation 20 by using the card swipe reader 23 located on the VEEBAAT verification workstation 20 that uses the VEEBAAT Verification Function (block 64). If Technologist B is unknown or does not have privilege to apply treatment, then the Verification Function will display a message on the VEEBAAT verification workstation 20 indicating the discrepancy. A Supervisor will be required to resolve this problem. Technologist B then views the scheduled Treatment Field Values for the patient at the VEEBAAT workstation 20 (block 66).

Figure 3C:
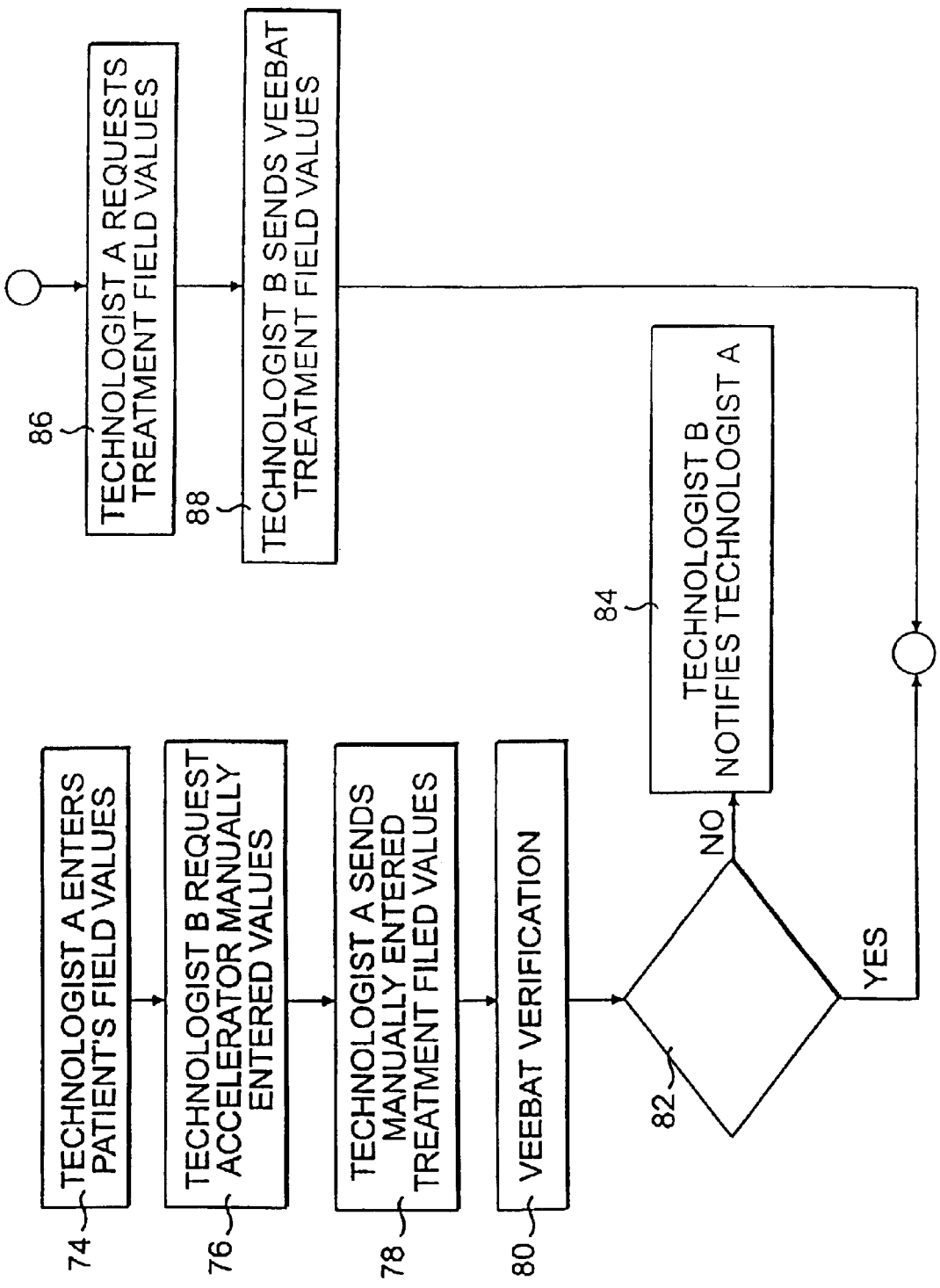

As indicated by decision diamond 68, and was discussed above, the VEEBAAT process can be configured for Manual Setup or Auto Setup. If the former confirmation is chosen, as indicated by block 70, the steps set forth at the left side of FIG. 3C are taken. Considering these steps, Manual Setup first requires that Technologist A manually enter Treatment Field Values as indicated on the patient's Treatment Chart at the accelerator workstation 26. The Treatment Field Values are then automatically verified at the VEEBAAT workstation 20 by the VEEBAAT Verification Function against the patient's prescribed treatment. As shown by block 74, Technologist A manually enters Treatment Field Values indicated on the patient's Treatment Chart at the accelerator workstation 26. Technologist B then places the VEEBAAT Verification Function in ready-to-receive mode. Technologist B verbally requests Technologist A to electronically send the patient's Treatment Field Values that were manually entered at the accelerator workstation 26 to the VEEBAAT workstation 20 (block 76). The accelerator (PRIMUS) workstation 26 electronically sends the data to the VEEBAAT workstation 20 when Technologist A presses a designated button (e.g., the "ACCEPT" button) on the accelerator keyboard (block 78). The VEEBAAT workstation Verification Function will only receive values from the accelerator workstation 26 when the VEEBAAT verification workstation is in the ready-to-receive mode. At any time, Technologist B has the option to cancel the ready-to-receive mode, thus returning the VEEBAAT verification workstation 20 to its previous state.

As indicated by block 80, the VEEBAAT Verification Function, after receiving the accelerator values that have been entered, will then verify all patient's Treatment Field Values and confirm that all values are within predetermined tolerances. If any Treatment Field Values are not within the predetermined tolerances, the VEEBAAT verification workstation will give an audio Warning Signal ("beep") and display an asterisk beside each field that is not within the predetermined tolerance. If all fields are within predetermined tolerance (i.e., when the output of decision diamond 82 is "yes"), the method or procedure continues as described below.

As indicated by decision diamond 82, if accelerator manual values are incorrect, Technologist B advises Technologist A to reenter any Treatment Field that was flagged at the VEEBAAT workstation with an asterisk (block 84). The processing is then repeated. If Technologist A intentionally enters in a value that is not consistent with the predetermined tolerance for any of patient's Treatment Fields, a Supervisor override is required.

Referring to the right side of FIG. 3C, the Auto Setup configuration electronically sends values from the patient's VEEBAAT Account through the VEEBAAT verification workstation 20 to the Accelerator workstation 26. In this regard, in the specific implementation under consideration, Technologist A places the accelerator workstation in a ready-to-receive mode by depressing a specific key (e.g., the F5 key) on the accelerator keyboard (not shown). Technologist A verbally requests Technologist B to electronically send the patient's Treatment Field Values(block 86). Technologist B, by depressing a download key, sends the requested patient's Treatment Field Values to the accelerator workstation 26.

It is noted that in accordance with a further aspect of the invention different tolerances are provided for Manual Setup and Auto Setup. In Auto Setup, relatively tight tolerances are provided so that, for example, the gantry angle tolerance may be ±1°. Although the automated operation has its advantages, it is important in some circumstances to provide a manual approach wherein the RTT manually sets the Treatment Field Values. Such a manual approach can be customized to the requirements of the patient over time and, in this regard, the Treatment Field Values may be changed over the course of treatment during the day. As a consequence, the tolerances set here should be relatively wider to accommodate the manual approach and, for example, the gantry angle tolerance may set at ±5°. Thus the VEEBAAT function provides a different set of tolerances for Manual Setup versus Auto Setup.

Figure 3D:
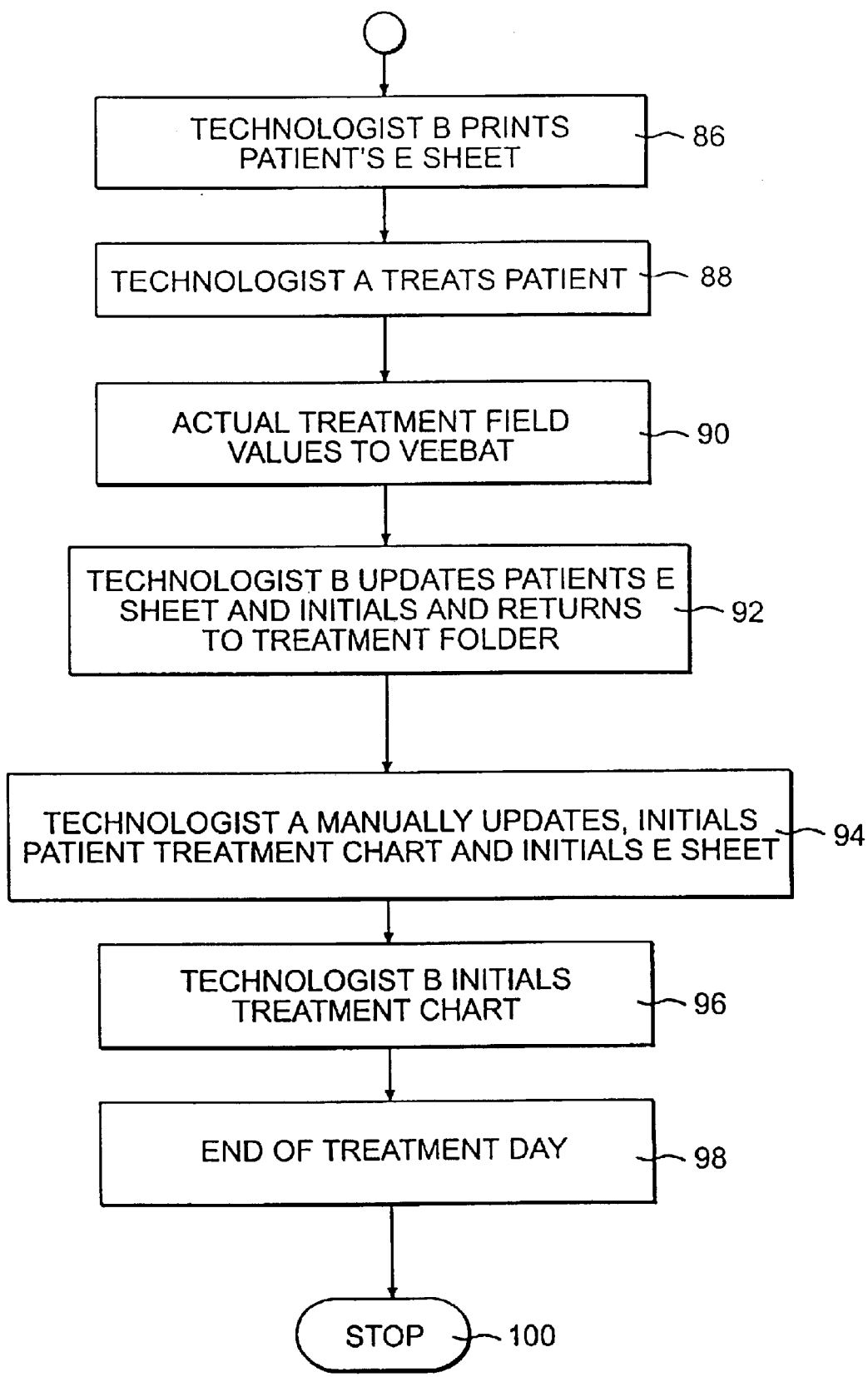

Referring to FIG. 3D, which depicts the remainder of the method or procedure, which is common to both the Manual Setup and Auto Setup, Technologist B requests the VEEBAAT verification workstation 20 to print a treatment entry on the patient's e Sheet at printer 24 (block 86), i.e., the date, energy, MU and wedge (i.e., the number of the wedge used, if any) for each prescribed/scheduled Treatment Field of the current treatment session. This occurs before the first treatment field for this treatment session. If this is not the patient's initial treatment session, the technologist will compare the printed values on the e Sheet to the previous treatment values (i.e. the line above on the chart). If the verification fails, a Supervisor is informed of any discrepancies.

As indicated by block 88, Technologist B next gives the Accelerator workstation 26 permission to treat the patient via the VEEBAAT verification workstation 20 and verbally informs Technologist A to proceed with treatment. If, during treatment, the accelerator 12 fails to give a complete treatment due to mechanical failure or technologist intervention, Technologist A may "fix" the problem and resume treatment until treatment is complete. However, if Technologist A is unable to complete treatment due to equipment failure or human decision, a Supervisor should, at a later time but prior to next treatment, manually write in the make-up dosage in the right margin of the Treatment Chart and override the patient's VEEBAAT Treatment Schedule.

Next, as indicated by block 90, the actual Treatment Field Values are sent to the VEEBAAT verification workstation 20 from accelerator workstation 26. The VEEBAAT Verification Function updates the screen with actual treatment dose delivered and saves the values to the VEEBAAT fileserver 30. If this is not the last treatment beam of the session, the technologists return to the treatment room and set up the patient for the next treatment field. If this is the last treatment, as shown by block 92, Technologist B submits the e Sheet to print the actual monitoring units (MU) on the same row of the e Sheet where the prescribed/scheduled Treatment Field Values are printed on the e Sheet in step 86 above. Thus, in a preferred embodiment, the e Sheet will include columns of entry spaces for the date, energy, wedge and MU, and for initialing by the Technologist or therapist. Such an e Sheet has important advantages because of its simplicity. An asterisk will be printed beside each Treatment Field that received a MU value outside the predetermined tolerance range. If one or more Treatment Field MUs were printed with asterisks, an asterisk will also be printed in the far right-hand column for the day's treatment. This asterisk indicates any discrepancies to the reviewing Physicist. Technologist B should initial the e Sheet at the appropriate session entry space and hand it to technologist A to initial and return to the patient's Treatment Folder (block 92). Technologist A enters the actual Treatment Field Values as shown on the accelerator workstation screen on the Patient's Treatment Chart (block 94). Technologist A then initials the Patient's Treatment Chart at the appropriate session line and hands it to Technologist B. Technologist B initials the Patient's Treatment Chart at the appropriate session line and returns it to the Patient's Treatment Folder (block 96).

Referring to block 98, at the end of the day, various reports can be requested. The reports are generated at a VEEBAAT verification workstation 20 using the VEEBAAT Administration Function. These reports can include a report of patients who received partial treatment. This report will list each patient that received a smaller dose for that day than was prescribed for that day. This report shall contain patient names and RT numbers.

The reports may also include a list of scheduled patients who were not treated. Such a report will list each patient who was scheduled for treatment that day but did not receive treatment that day for any reason. This report shall also contain the Patient names and RT numbers.

Statistics can also be output for the following treatment types: electron, photon, simple, intermediate and/or complex.

A billing summary can also be produced. This report will list charge codes for each patient treatment as well as patient's name, and concurrent chemotherapy or hormone treatments, if any.

A report can be generated on any information maintained in the VEEBAAT database which is located on Fileserver 30.

Considering in more detail the use of a photograph of the patient in generating distinctive audio output, in a preferred embodiment, a photograph of the face of the patient with an identifying barcode is taped or otherwise affixed to the inside front jacket of the Treatment Chart, although the photograph and bar code can take other forms and be printed or mounted on other media. When the chart photograph, with barcode, is scanned by the barcode reader of the corresponding laser verification station in question (station 14A in the example above), a suitable audio output which is uniquely associated with, i.e., specific to, the particular patient is emitted by the speaker (not shown) of the station. Conventional methods are available to generate a specific audio output in response to a corresponding triggering input, including computer generation of sounds or tones. As described above, verification station 14B is used to scan the patient's e sheet. In the specific exemplary embodiment under consideration, the audio output is an audio signal which takes about one second to complete. Of course, while a soothing tone sequence is preferred and has important advantages, other audio outputs can be used including a recording of the patient's name.

In an exemplary embodiment wherein three sequence of tones comprising the three tone chord is determined at simulation by the patient's RT number. For example, departments with different lengths of patient identifying numbers can adjust with a different range of octaves. Four digit departments can use a different octave for the first digit. Five digit departments can use a different octave for the first and second digit. Digits which begin with eight or nine can use sharps or flats as the first digit.

As indicated above, in the specific application under consideration, the second therapist, Therapist B, scans the patient's e Sheet at barcode reader 15B at laser verification station 14B located inside the treatment room on the opposite wall from station 14A, and a confirmatory audio signal emitted from the speaker 17B at station 14B is reassuring the staff that the Treatment Chart's face photo matches the e Sheet. This creates an opportunity to detect whether another patient's e Sheet has been inadvertently placed in the Treatment Chart. The audio signal emitted at station 14A obtained by scanning the patient's Treatment Chart should match precisely the audio signal emitted from the speaker 17B at station 14B. This process of scanning the Treatment Chart, producing a patient specific audio signal and then confirming the audio signal by scanning the e Sheet and producing the audio signal again is referred to herein as "echoing." Echoing is performed most efficiently when the e Sheet is scanned almost immediately after the Treatment Chart is scanned and thus generates its audio signal.

The sequence of Treatment Chart audio signal activation, followed by e Sheet tone activation, confirms that the Treatment Chart photo barcode is the same as the e Sheet barcode. If the wrong Treatment Chart is selected, the patient should notice a non-familiar audio signal, providing a self-managing dimension to the VEEBAAT process. Patients often report to their radiation oncology caregivers that they count the seconds of treatment or that they occasionally report perceived changes in the sound of the accelerator as it delivers the radiation treatment. The confirmatory audio signal should reassure anxious patients, while allowing an opportunity for wrong audio signal to be noticed by a patient. This provides an added incentive for the staff to select the correct Treatment Chart since the patient also participates in the cross checking process.

In accordance with a further feature of this aspect of the invention, subsequent fields will be confirmed by a repeat of the last tone and the next tone of the second field, the last tone and the two next tones for the third field, and the last tone and three consecutive tones for the fourth field. Variations of this tone feedback process could be used for three dimensional conformal therapy. Certainly, many patients are already primed for audible feedback and the use of audio confirmation should be of help to patients as well as the staff. The foregoing sequence of barcode scanning brings up the patient's VEEBAAT parameters which may then be downloaded for Auto Setup or Manual Setup, followed by verification before and after treatment as described above. This verification process provides a number of important advantages which will now be described.

First, two therapists are encouraged to enter the room with the patient and the Treatment Chart, maximizing the opportunity for satisfactory visual crosscheck. Both therapists are encouraged to enter the room because efficiency inside the room will be rewarded by bringing up the VEEBAAT parameters more rapidly, either for Manual Setup verification or Auto Setup. As indicated previously, two therapists are not required to enter the room but if only one therapist enters the room, she or he will still have to bring the Treatment Chart so that no charts will be left on the counter outside the treatment room. Moreover, the lone therapist will still have to set up the patient properly, then activate the VEEBAAT queue with the e Sheet at the right wall, i.e., at station 14B, as viewed in FIG. 1.

Further, with two therapists Therapist A must be with the patient at the left side of Accelerator 12 before the audio signal can be generated. The Treatment Monitor 16 and the VEEBAAT monitor 22 will display simplified patient parameters only after the e Sheet is properly scanned and the second audio signal is generated at station 14B. Typically, the simplified parameters are defined as a field number, i.e., 1) AP pelvis/prostate, 2) R lat pelvis/prostate, 3) PA pelvis/prostate, and 4) L lat. If Auto Setup has been approved by the Radiation Oncologist for the treatment of the patient, then treatment monitor 16 (in treatment room 10), and VEEBAAT monitor 22 (on the treatment counter) will display the simplified patient parameters with, e.g., red letters. If the patient is being treated using Manual Setup, then the corresponding screens will display the simplified patient parameters with different, e.g., white, letters.

Because the display will also appear on VEEBAAT monitor 22 at the treatment counter in area 18 which is not in treatment room 10, this provides advanced queuing for treatment, thereby minimizing delays outside the room due to delays in calling up the parameters after the patient's alignment has been visually cross-checked.

In an advantageous implementation, patients are assigned a new RT number and bar code for each course of radiation therapy. In an advantageous implementation, if a patient returns to the radiation oncology department in the future, e.g., for a second course of radiation therapy several years in the future, a fourth note will be added before the three-tone chord assigned for the current year, creating a new four-note chord. This serves as an audible reminder to the staff that the patient has had a previous course of therapy, and that they should watch our for possible overlap of the current field with the prior fields. A third course of therapy will generate a fifth note. In other words, in this implementation, there will be two tones, followed by a pause, followed by the three-tone chord for the current course of radiation treatment. It is more difficult to audibly discriminate longer sequences of tones, and this approach takes advantage of this. The greater the number of prior courses of radiation the patient has had in prior years, the more difficult it is for the therapist to feel comfortable with alpha-beta confirmations, and the more motivated he or she will be to go back to the records to verify lack of overlap with the current fields.

One very important advantage of the verification method and system of the invention is that its primary method of supplemental communication is audio, thereby eliminating the use of additional visual distractions that might divert the attention away of the therapists from the patient's Treatment Chart and actual treatment setup and visual cross-check. This approach also provides for more efficient queuing of the server verification data to the monitor outside the treatment room, so as to provide time for therapists to perform an official verification, followed by treatment, immediately upon reaching the treatment counter or console. Overall, the invention should make treatments faster and more accurate than with existing record and verify systems, because the invention enhances and verifies efficient manual process without altering therapist behavior.

GLOSSARY

| Term | Definition |
| --- | --- |
| Accelerator | The actual accelerator located in the treatment room. |
| Accelerator System | The Accelerator Workstation and the Accelerator. |
| Accelerator Workstation | Part of the Accelerator System, Consists of monitor, special keyboard, and computer. Location is outside the room of the Accelerator. |
| Auto Setup | The Accelerator System receives its Treatment Field Values from the Auto Download Verification Function |
| Bar Code | A label on the Polaroid Photo and e Sheet used to identify electronically the patients VEEBAAT Account. |
| Card Swipe | Device used to identify user by badge number |
| Cumulative Dose | Total Radiation received |
| e Sheet | Verification sheet used by Technologist during treatment showing scheduled and actual treatments |
| Error Signal | Audio tone emitted from VEEBAAT Workstation when an error requiring a Supervisor is required. |
| ICD-9 Codes | Used to categorize patients cancer location |
| Laser Verification Station A | A verification station located in the treatment room. Consist of a bar code reader and a speaker. Used by Technologist A to read a patients bar coded Patients Chart. |
| Laser Verification Station B | A verification station located in the treatment room consisting of a bar code reader and a speaker. Used by Technologist A in reading a patient's bar coded Patients Chart. |
| Manual Setup | The Accelerator System receives its Treatment Field Values from the Accelerator Workstation |
| MU | The length of a treatment (Monitor Units). |
| Patients File | Patients Treatment Chart, e Sheet, and Polaroid Photo |
| PC | Personal Computer. |
| PVF | Port Verification Film |
| Polaroid Photo | Picture of Patient |
| Radiation Oncologist | Physician |
| Red Folder | A patients folder until treatment is determined |
| RT | Radiation Oncology Number. |
| RTT | Radiation Therapy Technologist |
| RTT | Radiation Therapy Technologist (Technologist) |
| Setup Room | Room where Technologist A and B run the Accelerator and VEEBAAT Systems |
| Radiation Oncology Consultation | Work done with the simulator to determine a patients treatment |

-continued

GLOSSARY

| | |
|---|---|
| Supervisor | Senior Radiation Technologist |
| TCP/IP | Network communication protocol. |
| Technologist A | Technologist responsible for VEEBAAT Verification during treatment. |
| Technologist B | Technologist responsible for Accelerator Workstation during treatment. |
| Total Dose | Total prescribed dose |
| Treatment Field Values | Actual fields used by the Accelerator and verified by the Auto Download Verification Function. See Appendix A for list. |
| Treatment Folder | Folder used by Technologist during treatment |
| Treatment Monitor | A monitor located in the treatment room used to show a patients name and Treatment Field Values |
| VEEBAAT Account | Electronic data entered via VEEBAAT Workstation with VEEBAAT Administration Function. |
| VEEBAAT Administration Function | A program running on a VEEBAAT Workstation. The program is used to create and access patients VEEBAAT accounts stored on the VEEBAAT fileserver. The program also provide various report generation functions and administrative functions (i.e. System Backup) |
| VEEBAAT Fileserver | A workstation with houses the VEEBAAT Database. |
| VEEBAAT Process | Verify Easily Electronic Before and After Treatment Process |
| VEEBAAT System | The actual components used to implement the VEEBAAT Process |
| VEEBAAT Verification Function | A program running on a VEEBAAT Workstation. The program is used to provide a verification before and after treatment |
| VEEBAAT Workstation | A workstation with monitor, keyboard, mouse, CPU, bar code reader, and card swipe. The workstation provides the VEEBAAT Administration and/or Verification Function. |
| Warning Signal | Audio tone emitted from VEEBAAT Workstation when an error occurred but does not require a Supervisor. |
| White Folder | A patients permanent folder during and after treatment |

Figure 4:
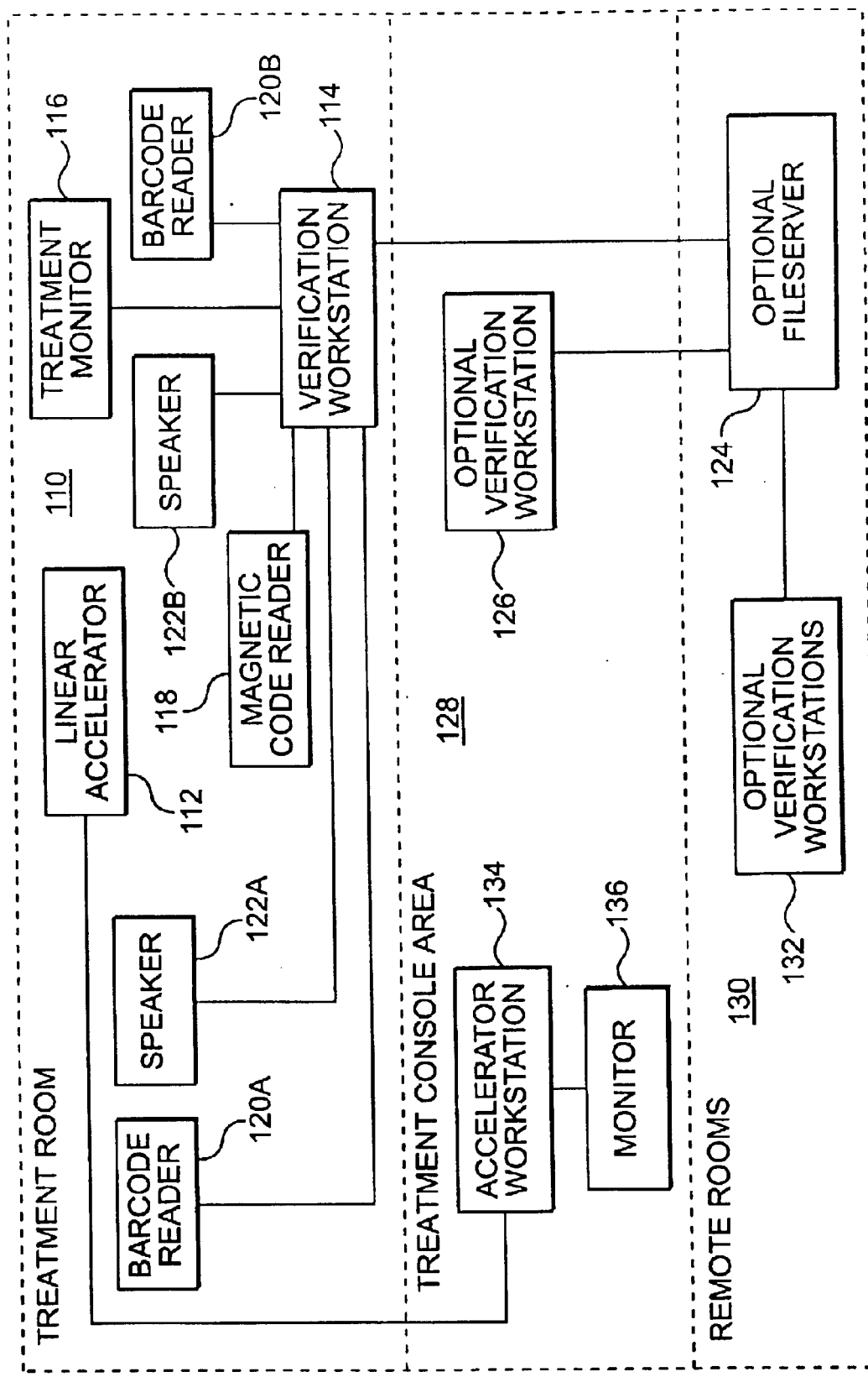
FIG. 4 is a block diagram of a further embodiment of the verification system of the invention as employed in a radiation therapy setting.

Referring to FIG. 4, a block diagram is provided of a further preferred embodiment of the overall system. The system is similar to that of FIG. 1 but incorporates a number of differences as discussed hereinafter or as will become apparent. A treatment room 110 includes a conventional linear accelerator 112 which administers the radiation treatment to the patient and which can be any conventional analog or digital system. A single verification workstation is provided in the treatment room 110 which is comprised of the following components which are not specifically illustrated: a computer processor, a keyboard, and a mouse. The workstation 114 also includes a monitor 116, a single magnetic code reader 118 located at the verification workstation 114, and two sets of barcode readers 120A, 120B and speakers 122A, 122B. In a preferred implementation of this embodiment, each set of barcode reader pairs 120A, 120B and speaker pairs 122A, 122B are located in the treatment room 110 across from each other. In other words, barcode reader 120A and associated speaker 112A are located on one side of the room and barcode reader 120B and associated speaker 122B are located on the other side of the room. An optional fileserver 124 is located in a remote location so as to enable the use of a client-server based system and permitting an optional verification workstation 126 to be located in a treatment console area 128 or other areas or remote rooms 130 as indicated at 132. This enables carrying out of system administration activities, initial patient registration, and report generation but not treatment activities. In the treatment console area 128 are located a conventional accelerator workstation 134 and an associated monitor 136.

With the setup illustrated in FIG. 4, the first technologist, Technologist A, is able to swipe his or her unique ID badge at the magnetic code reader 118 located at the verification workstation 114 inside the treatment room 110, registering the technologist as the "treatment" technologist. The second technologist, Technologist B, is then able to swipe his or her unique ID badge at the magnetic code reader 118, registering the technologist as the "verification" technologist. Technologist A is then able to scan the patient photograph at the barcode reader 120B located near the verification workstation 114. At this time, the system will determine if the "Auto Setup" treatment described above is permitted. Access to the Auto Setup features of the workstation 114 is only allowed if both technologists have privilege for Auto Setup and if Auto Setup is approved for the treatment of the patient. This is determined by the Radiation Oncologist and configured during initial patient registration. Next, the patient is set up at the linear accelerator 112 and oriented properly on the treatment table. Technologist A then scans the patient photograph a second time at the barcode reader 120B, thereby generating the patient unique audio signal. Technologist B then scans the patient's paper verification sheet (referred to above as the electronic sheet, or e-sheet or check sheet) at the opposite barcode reader 120A, thereby again generating the patient unique audio signal.

The verification process described above in connection with FIG. 4 provides a number of important advantages. First, the therapist(s) are required to enter the treatment room with the patient since the only verification workstation permitting treatment set-up, viz., verification workstation 114, is located inside the patient treatment room 110. Having both therapists inside the room maximizes the opportunity for satisfactory visual crosschecks. Second, the patient's chart and photograph must be taken into the room since these items are required to gain access to the verification workstation. Together, these two items are the key to establishing a "default to a safe mode of operation" process or situation. In other words, with the patient's chart in the therapist's hands and the therapist(s) inside the treatment room during the critical patient set-up period, the therapist(s) are given the opportunity to detect their own errors.

Figure 5:
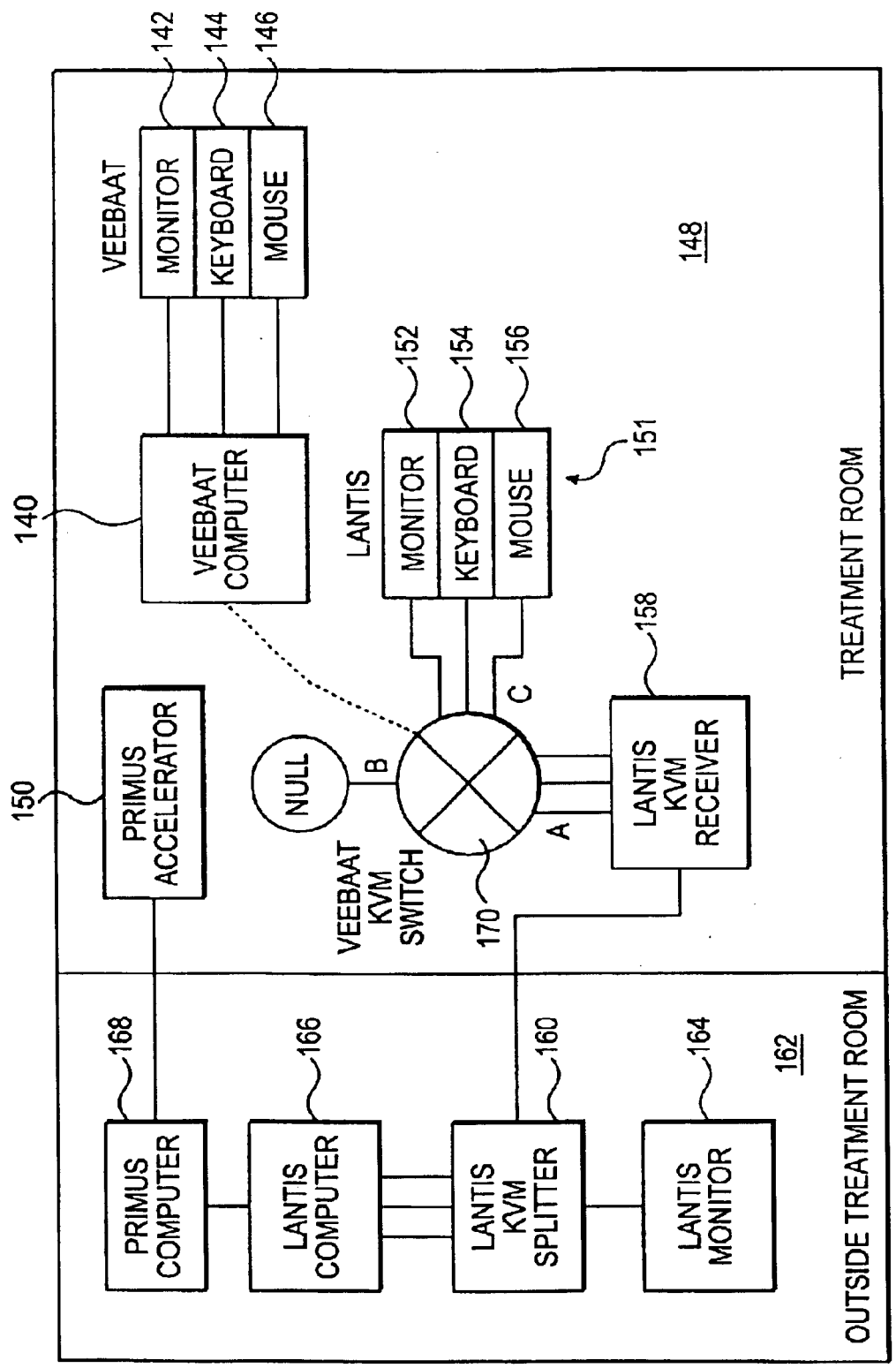
FIG. 5 is a block diagram of yet another embodiment of the verification system of the invention as employed in an access control mode.

In another preferred embodiment, shown in FIG. 5, the system of the invention is utilized with an existing auto-download treatment system (such as LANTIS, IMPAC, or VARIS) in a standard treatment facility. The system of the present invention is indicated in FIG. 2 as the VEEBAAT system, which as indicated above, is the trademark used to identify the system, and includes a computer 140, a monitor 142, a keyboard 144 and a mouse 146. The conventional system includes, in the treatment room 148, a PRIMUS accelerator 150, a LANTIS auto-download unit 181 including a monitor 142, keyboard 154, mouse 156, and LANTIS KVM (keyboard, video, mouse) receiver 158. The latter is connected to a LANTIS KVM splitter 160 which is located in an area 162 outside of treatment room 110 which is, in turn, connected to a LANTIS monitor 164 and to a LANTIS computer 166 connected to a PRIMUS computer 168 which controls accelerator 150. The existing auto-download treatment system communicates with the accelerator's computer to automatically pass patient treatment parameters prestored in a database to the accelerator 150 in the place of requiring these treatments to be entered manually by the technologist.

In the configuration shown in FIG. 5, the system of the invention can be utilized to prevent access to the auto-download system unless a particular set of criteria are met. The criteria are as follows: both technologists must log into the VEEBAAT system, both technologists must have permission to utilize the auto-download system (and as indicated above, this is a configurable item defined within the VEEBAAT program), the ICD-9 code (a code which defines the type/location of the cancer) must be configured to allow auto-download (also a configurable item defined within the VEEBAAT program), and the patient must be configured to allow auto-download (another configurable item with the VEEBAAT program). If any of the criteria is not met, access to the existing auto-download system is not allowed. All of the configuration items are controlled within the control system of the invention and can be altered by an administrator who has been given permission to access/alter these settings. The system of the invention also includes a built-in access level security system which enables tailoring authority or permissions for given users of the system. By controlling these configuration items, the treatment facility may limit the use of the auto-download system to individual technologists, individual ICD-9 codes, individual patients, or any combination of the three, as desired.

Access to the auto-download system is controlled by an electronic KVM (Keyboard, Video, Mouse) switch 170 and controlled by computer 140. The KVM switch 170 is located between the auto-download computer 140 and the auto-download unit 151 comprised of monitor 152, keyboard 154 and mouse 156. The computer 140 of the system of the invention controls the switch 170 via an RS-232 serial connection and enables/disables the auto-download system (keyboard/video/mouse) unit 151. The auto-download system is connected to Port A of the switch 170. Port B is left unconnected. When the switch 170 is positioned to Port A, access to the auto-download system is permitted. When the switch is positioned to Port B, access to the auto-download system is prohibited.

The system of the invention allows access to the auto-download system when all the required criteria have been met. If the criteria are not met, access to the auto-download system is prevented, thereby forcing the technologists to treat the patient in manual mode and enter the patient treatment data manually into the computer 168 associated with the accelerator 150. If the criteria are met, access to the auto-download system is permitted and the technologists can then load the patient treatment information from the database and auto-download it to the accelerator computer 168. With this configuration, the auto-download system (i.e., the monitor 152, keyboard 156, and mouse 156) is located inside the treatment room alongside the VEEBAAT system (computer 140 and monitor 142, keyboard 144 and mouse 146). This configuration forces the technologists to enter the treatment room with the patient chart. The technologists are therefore forced into a process which "defaults to a safe mode of operation" should a system failure occur, since the patient chart is required to gain access into the VEEBAAT system and VEEBAAT access is required to gain access to the auto-download system.

In accordance with yet another embodiment of the invention, the invention is used to assist verification of medications to be taken by a patient in a hospital or like patient treatment setting. In this embodiment, a laser barcode scanner or like detector or reader, and an associated speaker, corresponding to those described in connection with previous embodiments, is located near or at the bedside of a patient and preferably mounted on the wall. In addition, software is used which generally corresponds to that described above but which is adapted, and simplified, to carry the functions described.

In use of the system of this embodiment, the physician first writes an order for medication in the patient's chart. The pharmacy within the hospital receives the order for the particular patient and dispenses medication assigned to, i.e., in association with, a patient specific bar code assigned to that patient. In other words, the medication is dispensed in a packet, bottle, carrier, container or the like, with the patient specific barcode thereon.

Next, the bar coded medication is picked up by or delivered to a nurse or other authorized medical practitioner who brings the medication to the patient's beside along with the patient's medication sheet.

In the next step, the nurse scans his or her badge or activates his or her user identifier. Then the nurse provides that the medication sheet is scanned by the scanner or reader, followed by the patient's wristband, and a patient specific tone sequence is emitted based on the barcode on the sheet. The nurse then provides scanning of the medication container or carrier (for example, an I.V. or bar-coded pill dish) so as to generate a matching tone sequence so that the nurse knows that the medication container barcode and medication sheet barcode match. As indicated above, the patient will learn to recognize his or her patient specific tone sequence, i.e., recognize a particular sequence as being uniquely his or hers. Moreover, the nurse will be aware that the patients will learn their specific tone sequence, and thus there is an increased incentive for the nurse to verify that the medication is correct.

When the tone sequence is matched and identified, the patient takes the correct medicine. The system also records and verifies that the correct medicine was given to the patient.

In a further implementation of this particular embodiment, the system is used to assist in identifying authorized personnel assigned to a neonatal nursery and to verify that these personnel are authorized to care for infants, while also creating a verified data record. The only additional equipment to that just described needed is a scanner unit in the newborn nursery.

In this implementation, the identifying audio signal which is specific to the patient (again, preferably a three note chord played in sequence) is assigned to the mother in labor. When the baby is born, the baby is also assigned a unique identifying tone sequence which is generated in response to scanning a barcode carried by the baby's name card on the baby's bassinet. In the case of multiple live births, each baby receives a unique identifying tone sequence. For example, the same chord could be used but with a different suffix or ending (e.g., chord-one, chord-two, chord-three).

The nurse must have a barcode bearing badge and when the nurse takes the newborn from the mother, the nurse's badge is scanned by the nurse through the barcode scanner, followed by scanning of the baby's name card from the bassinet and next followed by scanning the baby's barcode on a wristband or legband, and the baby's three-tone sequence is generated after all of these scanning operations are completed and playing of this sequence confirms that the nurse is authorized to take the baby to the nursery. It is noted in contrast to an alarm or the like, the tone sequence is soothing and reassuring.

When the nurse, baby and bassinet arrive at the nursery, the nurse scans her barcode badge, followed by the bassinet barcode on the bassinet. The corresponding three tones, i.e., the three tone chord, will then be generated, confirming that the assigned nurse for the infant brought the infant into the nursery. The basic program or process verifies and then records in the database the various events that occur and the time at which the events occurred.

When it is time for the nurse to take the baby from the nursery to the mother's room, the nurse scans her bar coded badge through the scanner at the nursery, followed by the baby's name card on the bassinet. Again, the three tones are emitted, indicating that an authorized nurse is taking the infant from the nursery.

In accordance with a further embodiment of the invention, the invention is used to assist verification of medications to be taken by a patient on an outpatient basis. In this embodiment, which is illustrated schematically in FIG. 6, a laser barcode scanner and speaker unit 180 similar to those described above (or an equivalent unit,) are located in the patient's home, indicated at H, and linked to a modem 182 to be monitored by a home health agency or to function with a modem as a "stand-alone" in conjunction with a portable computer 184 such as a personal data assistant (PDA) or a pocket computer. The tone recognition software generally described above would be installed on computer 184 and would be programmed to recognize the barcodes on the patient's medication bottle, packet, pill box or like container or carrier. In an advantageous embodiment, further programming would include a medication scheduler which would provide feedback to the patient about timing of the medication to be taken. For example, the program could provide for emitting the patient's identifying tone when the medication container has not been scanned within a predetermined period (e.g., two hours).

Figure 6:
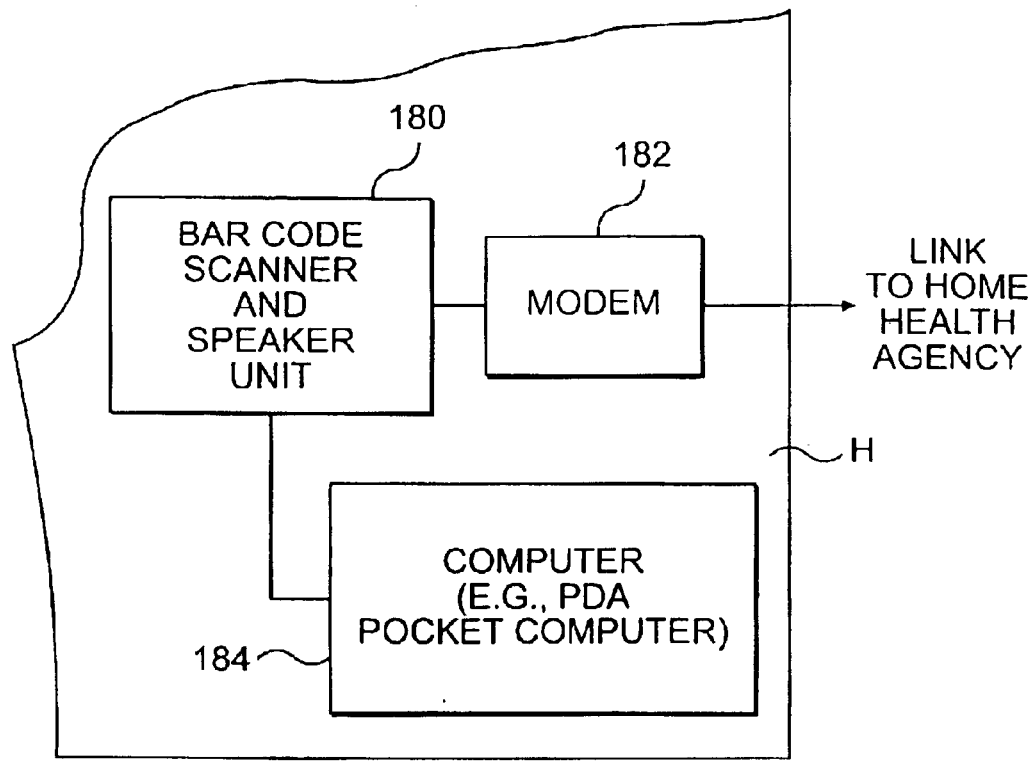
FIG. 6 is a block diagram of a still further embodiment of the verification system of the invention.

In operation, the process would begin with the treating physician writing an order for medication on the patient's prescription. The pharmacy would receive the order for the patient and dispense the medication as assigned to a patient specific barcode on the medication container. The container with the barcode would then be given to the patient. The patient would take the bar-coded medication container to the scanner unit 180 and provide for scanning thereof. A tone sequence or like audio signal, specific to the particular patient as described above, would be emitted thereby indicating that the medication container had not been scanned in the past, e.g., two hours. In an advantageous embodiment, the system would be programmed to provide specific time window guidance as to the taking of the medication, i.e., guidance as to what medication was to be taken and within what time window, with tolerances being programmed in based on input from the pharmacist or health care provider. In any case, the program in computer 184 records and verifies that the medication container was scanned by the patient and records the medication and the time of day for later reporting. If, as shown in FIG. 6, the system is linked by modem 182 to a home health agency, the report can be sent automatically to the responsible parties via a cordless telephone link.

It will be understood that while in the foregoing description, patient photographs and other patient identifiers are used on the source document or card carrying the barcode that is scanned to call up the patient record and/or the audio signal file, other identifiers, which are individualized for a particular patient, can also be employed. Further, while including both a patient photograph and barcode on the patient card has obvious advantages, a single patient identifier can be used, for example, to call up the audio signal file containing the audio signal assigned to the particular patient. Other patient identifiers or identifying processes that can be used for this purpose, and other purposes, include retinal scanning, fingerprint scanning, iris scanning and subcutaneously implanted microchip scanning for individuals who request and consent to such devices for medical care reasons. The patient identifier would be scanned or read by a scanner or reader, preferably located in the treatment room as previously described, so as to trigger the playing of the patient specific audio signal when a patient identification or patient match was established by the scanning operation.

Figure 7:
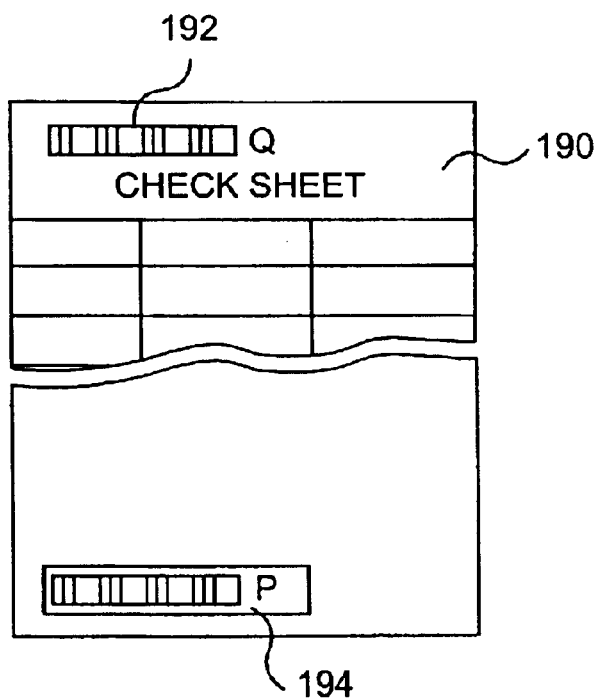
FIG. 7 is a plan view of a check sheet in accordance with a further aspect of the invention.

Turning to yet another aspect of the invention, although a check sheet as described above can be used in the various applications of the invention (after suitable modification to adapt the sheet to the particular application), in accordance with this further aspect of the invention, an improved check sheet is provided which is shown schematically in FIG. 7 and is generally denoted 190. As shown, the check sheet 190 has a first barcode 192 at the top middle portion of the check sheet, and a second barcode 194 at the lower left portion of the check sheet. As discussed above, a check sheet functions in radiation therapy as a manual quality assurance tool in real-time. In the illustrated embodiment, the barcode 192 is fixed to the top of the page and contains the patient's radiation therapy (RT) number with a Q suffix. In contrast, the barcode 194 is removably affixed, e.g., by an adhesive, is located at the lower left corner of the check sheet 190 and contains the patient's RT number with a P suffix. Barcode 194 can be peeled from the check sheet and applied to, i.e., stuck on, the patient's identification photo, chart, identification card or identification band at the time of simulation (e.g., virtual, fluoroscopic, clinical).

When the applied stick-on barcode 194 (photo, chart, I.D. card or patient band) is scanned, the patient's personal audio signal file is activated, i.e., made audible. As indicated previously, in a preferred embodiment, the audio signal is known and recognized by the patient and the radiation therapy technologists (R.T.T.s) or other medical practitioner or caregiver. Scanning the fixed barcode 192 at the top of the check sheet 190 generates the same audio signal, confirming that the stick-on barcode 194 matches the fixed barcode 192 at the top of the check sheet 190. The check sheet 190 can be used in in-patient medication delivery and infant identification such as those described hereinabove, with I.D. bands, cards, badges and medication check sheet verification. The check sheet 190 can also be used in the outpatient medication compliance system discussed previously.

The check sheet 190 minimizes the potential for mismatched barcodes because it can be assured that the patient's number is the same on both barcodes 192 and 194. Use of check sheet 190 is a one-step procedure which optimizes the probability of correctly applying the peeled barcode label to the correct patient record. The check sheet serves as an additional safety net in the event other verification systems are inoperative.

The invention has principally been described above with respect to the application therefor to radiation therapy and although other applications have also been described, there are still other applications of importance. One of these is in the field of chemotherapy. The system used for this application would include anywhere from one to many individual stations. The hardware used in a typical station of such a system is shown in FIG. 8 and is comprised of a computer 200, a touch-screen monitor 202, a keyboard 204, a mouse 206, two speakers 208 and 210, a barcode scanner 212, a laser or dot-matrix printer 214, and a barcode printer 216. In an advantageous implementation, all of this equipment is located on a single computer stand (not shown). The laser/dot-matrix printer 214 is used for printing of reports generated by the computer program. The barcode printer 216 is used in printing of barcode labels for new patients to be treated.

Referring to FIGS. 9(a) to 9(d), there are shown the basic steps in a preferred embodiment of the treatment verification and record method of this aspect of the invention. However, before considering FIGS. 9(a) to 9(d), it will be understood that when a new patient is to receive chemotherapy, the process begins with assembly of a new patient chart. The steps involved are as follows:

Patient information (name, ICD-9 diagnosis, and so on, as required) is entered into the computer 200 for the new patient.

The barcode printer 216 print out two barcode labels for the patient, one for the front of the patient chart and the other to be placed on the patient "flow sheet" (which is equivalent to the "check sheet" described above). This enables the system to later verify that the patient chart and the flow sheet always belong to the same patient.

The laser printer 214 prints out labels for the drug syringes used in the chemotherapy process. A nurse indicates how many treatments are planned for the patient and printer 214 prints out the complete set of labels for all treatments for this patient. Pre-printed labels are then placed inside the patient chart. In this regard, one label is used for each treatment session as the chemotherapy drug is prepared and placed into the syringe for the patient. The printed label includes the patient name and, in a preferred embodiment, a barcode as well so as to allow the system to later verify the patient chart, flow sheet, and syringes all are for the same patient just prior to treatment delivery.

Turning now to FIGS. 9(1) to 9(d), in a first step (block 220), the patient arrives for treatment. Although the next step (block 222) may have been done hours earlier in the day, the patient chart is pulled and treatment information obtained. In the next step (block 224), the syringe filled with appropriate chemotherapy drug and the pre-printed label described above is placed on the syringe.

As a next step (block 226), the patient is taken to a treatment room.

In the patient room, the nurse enters treatment room with patient chart (block 228) and scans chart barcode (block 230) and flow sheet barcode (block 232). The patient specific audio signal is generated at, in this preferred embodiment, the left speaker 208 (block 234) thereby allowing the patient to verify that it is their chart. The system also verifies on the screen of computer 200 that the two barcodes correspond to each other, i.e., that the patient chart and flow sheet are for same patient. The actual sequence preferably provides that the nurse select a treatment chair or regime from the touch-screen monitor 202 and indicate that a new patient has arrived for treatment, followed by the two barcodes being scanned and the matching audio signal being generated. At this point, the system would then display the patient name to the nurse, thereby providing a visual verification of the patient name.

In the next step, indicated by block 238, the patient is hooked up to an IV and some pre-treatment drugs administered. These drugs are anti-nausea, dehydration and like drugs. In one implementation of this embodiment of the invention, these drugs are also barcoded as well and are scanned at a scanning station prior to delivery. This would aid in charge capture by providing all drugs that are delivered in connection with a procedure are scanned into the system.

In the next step (block 242), the pre-chemotherapy treatment is administered. The pre-treatment drugs are normally administered for approximately one hour. The nurse sets up a "timing bag" at the same time, which causes an alarm to go off when pre-treatment drug delivery is completed. To assist here, a countdown timer is advantageously provided so as to enable the nurse to get an overview of each patient, their treatment status ("pre-chemo" or "chemo"), and the time remaining. After hanging the timing bag, the nurse would just select the appropriate patient chair on the touch-screen 202 and start a countdown timer to provide an alert as well as an indication as to when the pre-treatment is completed. As indicated by block 244, the nurse would normally leave the room during this period.

Figure 9A:
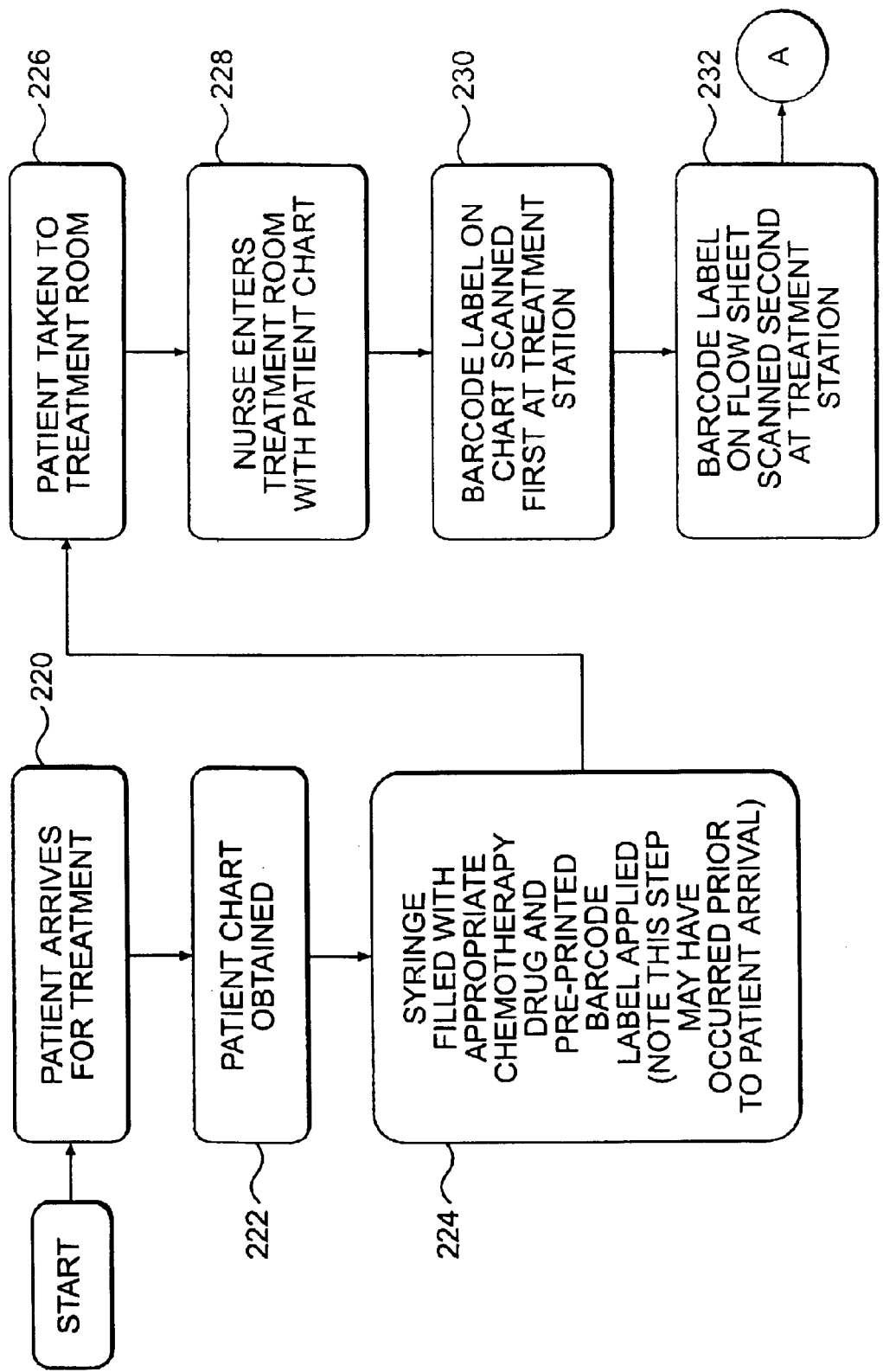
Figure 9C:
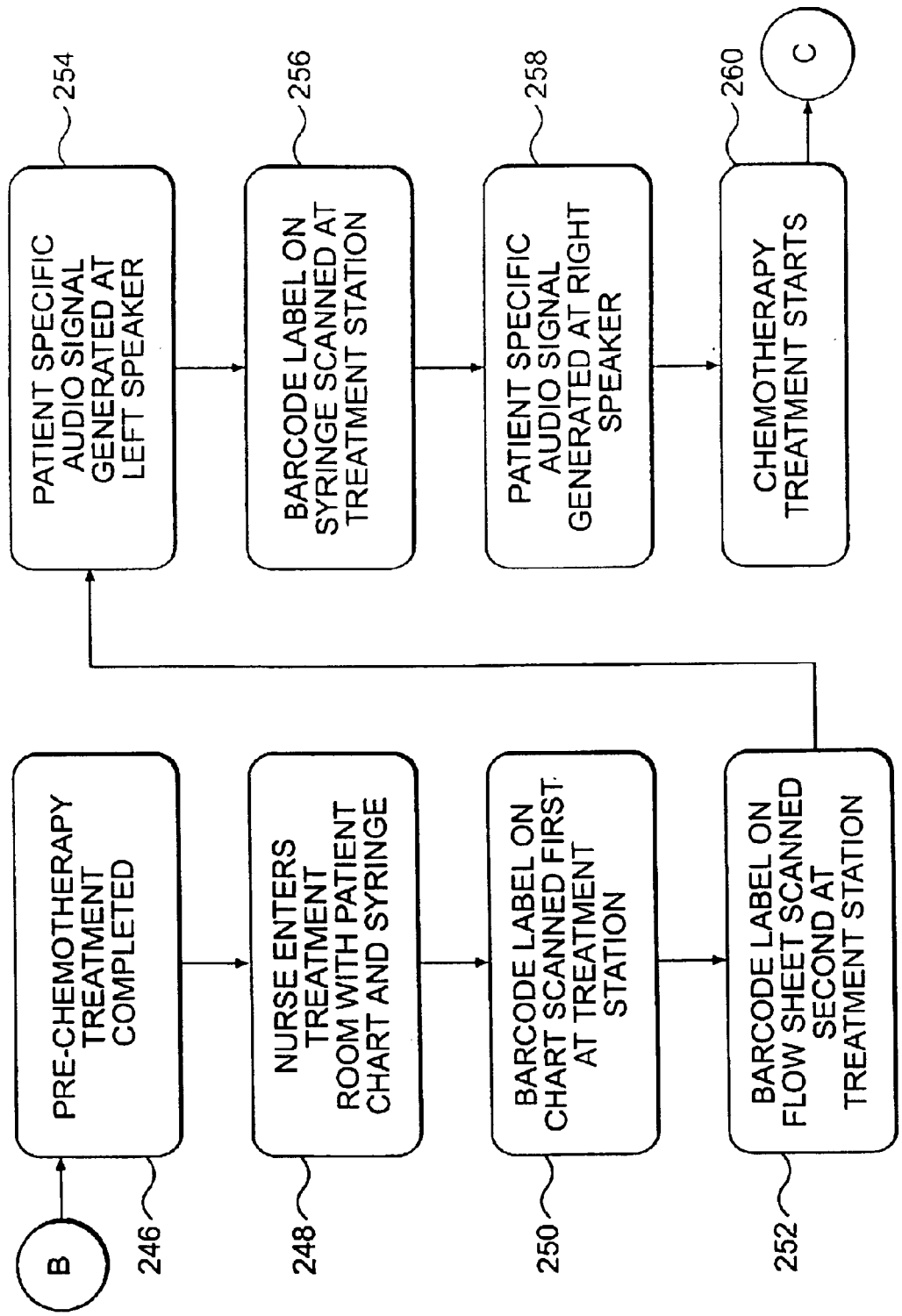
Figure 9D:
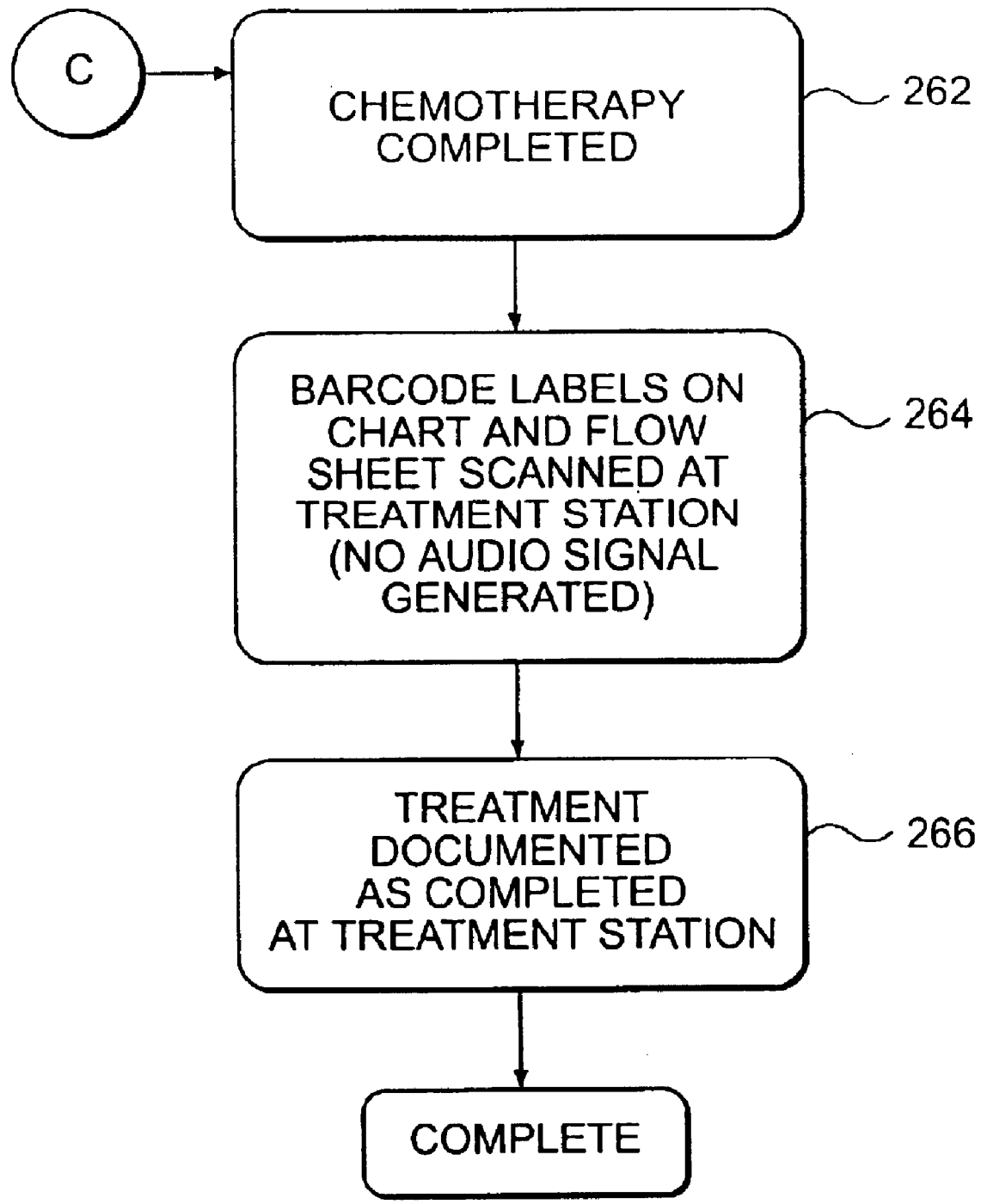

As set forth above, when pre-treatment is complete an alarm goes off. The nurse then retrieves patient pre-filled syringe and enters treatment room again with the patient chart (block 248). The patient chart, flow sheet, and syringe are scanned by scanner 212 and the patient specific audio signal is generated in response. More specifically, as indicated in FIG. 9(c), the barcode label on the patient chart is scanned first (block 250), the barcode label on the flow sheet is then scanned (block 252), and the patient specific audio signal is generated at the left speaker (block 254). The barcode label on the syringe is then scanned (block 256) and a patient specific tone generated at the right speaker (block 258) thereby enabling patient verification. This also verifies that all barcodes are assigned to the same patient and this, of course, includes the syringes. For high-risk patients (those with specific ICD-9 diagnosis or those flagged manually by the nurse during patient registration), the system also provides a prompt for a verification nurse to enter his or her badge or other identifier or initials at the station to indicate that someone has verified the drugs prior to administering the treatment. This simply adds an additional cross-check for high risk situations.

At this time, the nurse is able to start a countdown timer if desired for treatment delivery and the chemotherapy starts (step 260).

Once treatment is completed (block 262), the nurse selects a patient chair on touch-screen 202 and indicates that the treatment is completed. As indicated by block 264, the barcode labels on the patient chart and the flow sheet are scanned by scanner 212 but no audio signal is generated as this is not required for this step. A report can be generated at this time and printed in real-time to indicate the actual treatment given as well as the previous treatment history and the treatments remaining for the particular patient (block 266).

It will be appreciated from the foregoing that reports can be generated from the computer station indicating the particular patients that have been treated during a given time frame. The billing secretary can use this to verify that all patients treated for a given day were billed appropriately. In addition, in a preferred implementation, billing information is transferred electronically in real-time following treatment completion to a commercial medical billing software system across a network. This latter approach captures all chemotherapy charges electronically as they occur without requiring manual efforts alone, to track all of the billing.

It will be appreciated that all of the steps outlined above in connection with FIGS. 9(a) to 9(d) are not new and although a number of advantages of the invention should be apparent from the foregoing, it is believed to be helpful to contrast the treatment of FIGS. 9(a) to 9(d) with typical current treatment practice.

In a typical chemotherapy treatment, one nurse hand labels blank peel-off labels, and a schedule and chart are used to mix the required drugs. After the drugs are mixed, the syringe to be used is labeled with the patient name and the name of the drug (e.g., Adriamycin). The labeled syringe is placed next to the chemotherapy hood. The patient is next escorted into the infusion area and seated in the chair. Vital signs are taken and they are typically recorded on a blank scrap of paper for later transfer to the flow sheet of the patient's chart. The drugs (e.g., Zofran and Decadron) are started and during this period the nurse transfers the vital signs from the scrap of paper to the flow sheet. The "timing" bag drips in so as to delay the alarm referred to above and the infusion pump sounds the alarm when the bag runs out, indicating that it is time for the chemotherapy treatment to begin. At this point, the nurse hears the alarm and injects the syringe into the bag. The nurse uses then writes the drug name on the bag in "Sharpie" indelible marker, the bag is hung and the infusion rate is programmed into the pump. After the patient receives the infusion, the nurse or nurses must document the charges manually on several forms.

In the treatment method of the invention, the patient chart is used to mix the drugs and, as indicated previously, the registration process results in the printing of two barcodes, one for the chart and one for the flow sheet as well as the correct number of peel-off labels for the particular drug course or protocol. As set forth above, after the drugs are mixed, the syringe is labeled with a barcode label which includes the patient name, the name of the drug, etc. (e.g., "Jane Smith, Adriamycin, cycle 2 of 4" or "Jane Smith, Cytoxan, cycle 2 of 4").

The next part of the procedure is the same as in conventional treatment through the seating of the patient in the treatment chair. At this point, the front cover of the patient chart would be scanned and the audio signal generated in the left speaker. The chart is then opened, the flow sheet scanned and the audio signal generated in the right speaker. The vital signals are then taken and recorded in the chart on the flow sheet, in real time.

As in the currently used procedure, the drugs are then started and the "timing" bag infuses to delay the alarm, the infusion pump sounds when the bag runs out and the nurse hears the alarm indicating that it is time for chemotherapy to start. At this point, the nurse injects the previously labeled syringe or syringes into the bag which is labeled with a "Sharpie" marker as in the conventional process. At the end of the treatment, the nurse scans the patient chart and flow sheet and the above-mentioned billing prompt is generated (e.g., Bill patient? (Mrs. Jane Doe) yes/no). A positive response to the billing prompt generates a hardcopy sheet which is initialed by the nurse, signifying that the sheet agrees with the flow sheet and the signed hardcopy sheet is sent to billing.

In accordance with a further aspect of the invention, a medical billing system and method are provided which is specifically designed to ensure capture of charges that are sometimes missed or overlooked in billing for medical services. The system provides for logging in of the presence of a patient treatment chart or check sheet at a particular location such as a treatment room. The presence of the chart at that location can be determined, for example, based on an event involving the chart such as scanning of the chart by a scanning device at that location, as described above, or by using a tracking system which keeps track of the location of the document. When the patient treatment chart is determined to be located in the treatment room, the presumption is that the patient is being treated and thus that services are being rendered that should be billed for. By logging the presence of the chart at the treatment room into the billing system, the system is alerted to the fact that treatment has occurred or will occur and that a bill for the treatment should be generated. If no bill is generated, the billing system is queried as to why, and an inquiry is made.

Although the invention has been described above in connection with generating a characteristic audio signal in response to a match with an identifier, and this has important specific advantages, in an alternative embodiment, a visible indication or signal could be provided in a match situation, e.g., by energizing a light source. Further, a particular visual pattern unique to the patient and known to him or her could be generated in a match situation.

Turning to a more general consideration of the invention, it should be appreciated from the foregoing that the core method or process of the invention is not a primary verification tool. The invention serves to provide a secondary verification opportunity or documentation affirmation of other verification processes and does not replace or undermine other existing verification methods. One key difference between the invention and other systems or methods is that the invention enlists the patient in the identification process in a positive way. The enlistment is done in an aesthetically pleasing manner, with the above-described tones being emitted from the background. In this regard, it is noted that foreground stimuli would only further distract the caregiver and/or patient who is already bombarded by stimuli from numerous automated systems. Further, the invention does not contribute to automation induced user complacency because the identifying tone employed in the preferred embodiments of the invention, is a pleasing sound that differs from the beeps and alarms associated with other medical technologies which are designed on management by exception strategies. The system awards the user for doing the right thing, rather than penalizing the user for a misstep, which is how other systems work, and all this in view of the patient. Moreover, the tone is intended to provide specific reassurance, not alarm, in the listener. The invention preferably uses a database of protected audio files that produce a tone sequence specifically assigned to the individual patient. The listener then recognizes his or her tone chord on a long-term basis.

As more therapies move in the direction of chronic condition management as opposed to acute care management, the advantages of the invention will become even more apparent. This is particularly true in an environment noted for severe shortages in nursing personnel as well as in the area of high technology specialties such as radiation therapy, where new or temporary personnel are brought in to care for clients and patients with complicated chronic medical conditions. Delivering incorrect medication or treatments in highly specialized care settings can have a far more serious consequence in the medical environment of today than it would have just a few years ago. As treatments become much more tailored to an individual's disease or predisposition to a disease, the consequences of delivering even one wrong treatment may be far more toxic to the patient. Specific, targeted treatments often have a narrower therapeutic window, and may be beneficial only when delivered to a certain patient under certain conditions. The invention is flexible enough to be able to emit confirmatory tones under these refined scenarios, i.e., to confirm that the patient is the correct patient, the treatment chart is the right chart, and the sequencing or timing of the treatment is correct, and, as indicated above, this is all done in the background through the use of pleasant audio signals which can be recognized internationally, independently of language differences. It is noted that the chord sequences selected for international distribution could be derived from major chords for individuals of western background or a western country of origin, but could also be matched to the country of origin by using in the tone assignments, minor chords or other culturally more familiar chord-based tone sequences for individuals from non-western backgrounds or countries of origin. Further, a pre-chord sequence preferably provided that would serves as the geographic/year of origination of the tone assignment.

In some of the preferred embodiments of the invention described herein, two speakers are provided in the treatment room on opposite sides thereof. It has been found that "panning" of the audio signal across the room, i.e., playing the sound on one side of the room in response to a first scan and then playing the sound of the other side of the room in response to a second scan is advantageous. In this regard, panning helps with recognition of the audio match event, by differentiating the event from other sounds in the treatment room and by differentiating a repeat scan of the photo from scanning of the photo and then the check sheet. Preferably, the length of the tone chord is 2 to 3 seconds for a monosound setup and ½ to 2 seconds for the panning embodiments. These times are designed to provide the most efficient way to match task-critical entries in the shortest time and are based on maximizing discrimination based on tone contour and melody recognition.

It will be understood that a safety system ideally should be designed so that a successful recovery procedure can be implemented if the primary process should fail. The present invention does this because the invention serves to provide positive confirmation. In this regard, in a preferred embodiment, if the scanned patient or treatment demographics do not match, resulting in no tone sequence generation, the user hears nothing. The absence of the confirmatory tone sequence is what prompts the caregiver or patient to question the treatment that is about to be delivered. This is an important point because if the system of the invention should fail for any reason, the patient or caregiver is prompted by the absence of an audio confirmation to investigate further. The system of the invention is not an alarm that prompts the user to investigate because if the alarm should fail, the user does not know that the safety mechanism has failed. If the system is silent when a tone is expected, the user becomes more vigilant.

It will be appreciated that variations and modifications can be made in the specific exemplary embodiment of the cross checking method described above. One key feature of the overall method concerns the provision of the separate electronic check sheet or e sheet, also referred to herein as the paper verification sheet, and the separate entry of data into this check sheet. This exercise keeps focus of the therapists on the task at hand and reinforces the ideas of the importance of proper data entry. In one preferred embodiment mentioned above and described in more detail below, only a limited number of parameters are entered to the check sheet. This is preferably done prior to treatment whereas the patient treatment chart is preferably used as the true record of what was done.

In one other preferred embodiment which advantageously employs the features just described above, the following steps are employed:

(a) A first therapist, referred to as the treatment therapist, enters the patient treatment parameters (i.e., the prescription or treatment data) from the patient treatment chart into the treatment monitor (which includes a computer either as an internal part thereof or associated therewith) and which controls, through means of the computer, the treatment machine or unit. This step is not performed, i.e., the treatment parameters are not separately entered into the computer of the treatment monitor by the first therapists, if a conventional record and verify system auto-download is utilized, as the system will automatically transmit the patient treatment parameters, stored in the system, into the computer which controls the treatment machine, upon operator request.

(b) The treatment therapist recites aloud treatment data from the patient treatment chart.

(c) A second therapist, referred to as the verification therapist, verifies recited data against treatment machine computer display, i.e., the data displayed on the treatment monitor screen.

(d) The verification therapist recites aloud treatment data from treatment machine computer display.

(e) The verification therapist enters certain treatment parameters (preferably the three treatment parameters mentioned above and described below) into the paper check sheet or verification sheet.

(f) The therapists turn on the accelerator beam and treat the patient.

(g) The treatment therapist enters data corresponding to the actual treatment delivered into the patient treatment chart.

Steps (a) through (g) are repeated for each field. As will be understood by those skilled in the art of radiation therapy, a field is the area of interest that is being treated. A field usually consists of a specific area of the body that is involved in the malignancy and often encompasses the surrounding areas of potential spread for the malignancy. A field is typically named for the part of the body that the radiation beam enters. It will be appreciated that the beam is caused to enter different parts or areas of the body during a usual radiation treatment session, by moving the body relative to the beam, so that plural fields are typical.

Preferably, with plural fields, the treatment therapist enters the cumulative dose delivered to the patient into the patient treatment chart.

Advantageously, the treatment and verification therapists review, sign, and countersign the patient treatment chart and the check sheet.

After this, in a set-up where the treatment therapist and verification therapist are outside of the treatment room during this process, they enter the treatment room and assist the patient off the treatment table.

In the specific embodiments discussed above, two radiation therapists cross check the data entered into the patient chart and the check sheet. In accordance with a further implementation of this aspect of the invention, an improvement in the core cross checking approach is provided which concerns following a specific sequence in carrying out the basic cross checking functions. It has been found that following this sequence can be very helpful in assuring that the functions are carried out properly. As with any human endeavor, there is the possibility of human error whether resulting from inattention to the task at hand (resulting, e.g., from the people involved talking about other matters or a failure for other various reasons of either or both therapists to keep their minds focused on the task) or from other causes, and this aspect of the invention helps ensure that the proper focus is maintained.

Although this aspect of the invention obviously has broader applications, the method will again be described in connection with the cross checking procedure carried out by radiation therapists as just described above.

In a specific embodiment of the implementation, the method or procedure comprises the following specific steps:

(a) Both therapists initially view and focus on the monitor screen of the monitor for the control unit (e.g., a PRIMUS® controller) which controls the accelerator used in providing the radiation treatment.

(b) The first therapist reads aloud preselected parameters items from the screen which are most important in the radiation treatment. As indicated previously, in a preferred, advantageous embodiment, the following three pre-selected parameters are read out: (i) the status with respect to the presence or absence of a wedge or other beam modulator (i.e., "wedge in"); (ii) energy level; and (iii) monitor units (MU). As discussed elsewhere in this application, these parameters are of critical importance and, as described below, another aspect of the invention concerns providing a check sheet limited to these three treatment parameters. However, it will, of course, be understood that other parameters (e.g., field size, table position, etc.) can be included, and different combinations can be used, as desired.

(c) The second therapist, while still looking at the monitor screen, repeats the parameters, in real time, as read off by the first therapist.

(d) The second therapist, while still looking at the monitor screen, reads aloud the same preselected parameters from the screen.

(e) The first therapist, while still looking at the monitor screen, verifies the parameters, in real time, as read off by the second therapist. Of course, if a mistake is made in reading out the parameters, this is discussed and corrected.

(f) The second therapist looks down from the monitor screen and writes the parameters on the electronic check sheet or paper verification sheet. (The second therapist can, of course, check the screen, as needed, if necessary.)

(g) Treatment of the field is initiated (i.e., "beam on") and following treatment of the particular field, the first therapist will enter the parameters into the patient treatment chart.

(h) The procedure then goes forward as described above.

As indicated hereinabove, this method or approach to entry of data into the patient treatment chart and the electronic check sheet assists the therapists in fully and completely focusing on the task at hand and thus ensures that the critical entries are properly made into the chart and check sheet. The critical procedures includes verbal communications between the two therapists as well as performing the cross checks in real time. The electronic check sheet is updated immediately prior to treating each field and the patient treatment chart is updated immediately after treating each field, thereby providing an opportunity for the therapists to immediately detect any potential errors in the treatment parameters being administered.

As set forth previously, in accordance with a further important aspect of the invention, the electronic check sheet or paper verification sheet, lists only three pieces of data for final verification by the therapists prior to administering a treatment, viz., wedge presence, energy, and monitor units (MU). It will be appreciated that while there are typically dozens of treatment parameters that could be verified prior to administering treatment, verification of all parameters would be cumbersome and time-consuming. Of all the treatment parameters, the three included on the check sheet are believed to be the three most critical, i.e., these are the parameters that would cause harm to the patient if incorrect. In this regard, the lack of a wedge when one should be present would result in a treatment overdose. Further, the term "energy" refers to the intensity (voltage) of the radiation beam (with typical energy values being 6 or 10 MV (megavolts)) and an incorrect energy setting can result in either an underdose or overdose. Similarly, the monitor unit (MU) value is a calibration value related to the radiation dose delivered and refers to the monitor units used in programming a radiation therapy machine or unit for accurate dose delivery. Thus, as with the energy value, an incorrect monitor unit value or setting can result in either an underdose or overdose.

It should also be noted that the validation of these three treatment parameters together also help validate the patient identity, as it has been found that the three values together are statistically unique between patients. In other words, there is a very low probability that more than one patient under treatment at any given time would have the same three parameters values. Thus, validation of the three values helps verify the patient identity, assuming, of course, that the treatment about to be administered (as reflected in the check sheet) is correct for the patient.

Referring to FIG. 4, there is shown one embodiment of the patient treatment check sheet or verification sheet described above. As illustrated, the check sheet, which is denoted 102, includes four columns 104, each with a respective heading as follows: one heading, "DATE," for the current date, i.e., the date on which the check sheet 102 was filled out, and three headings for the three treatment parameters, viz., "WEDGE" for wedge presence, "ENERGY" and "MU" as explained above. A check-off column 106 can also be provided as well as check-off area 108 for enabling the two therapists to indicate that they have checked the entries, as explained above in connection with the cross checking procedure. Further, check sheet or log 102 also preferably includes a patient identifier (barcode) 107 for scanning, as described above, to generate the patient specific audio signal.

Turning to a further aspect of the invention, although the invention is obviously not limited to this implementation, in one preferred embodiment described above, the audio signal provided is a short series of tones or a short bar or portion of music which is assigned to the patient and which can be identified by the patient when the audio signal is generated in response, e.g., to reading of a bar code on a patient treatment chart. In accordance with a further aspect of the present invention, a further separate audio signal is generated, preferably after the playing of the initial patient specific signal, which continues during treatment until the attending treatment personnel (e.g., the treating therapist or therapists) log off the associated computer system. Although the further audio signal is preferably generated after the generation of the first patient specific signal, it is to be understood that this aspect of the invention can be practiced alone, i.e., apart from the generation of the first signal.

Considering this aspect of the invention in more detail, the further audio signal is also specifically assigned to a patient and, in an advantageous embodiment, the initial audio signal and the further audio signal are related. For example, the further audio signal can be a song or other pleasing and/or soothing piece of music and the initial signal can be a short excerpt from (or some other part of) the song or other music. The further signal is generated so as to loop, i.e., play on a continuous basis, until log off occurs. The patient is familiarized with and ultimately knows his or her music and is instructed not to get off of the treatment table until the further audio signal (e.g., song) is over. Before log off can occur, it is necessary for the attending treatment personnel to enter all charges for treatments for the patient that have been carried out and to perform whatever final checks that are required. With this approach, the treatment personnel will be motivated to promptly complete the treatment procedure, including all charge capture, so as to be able to log off and thus to free up the treatment room for the next patient. In this way, this aspect of the invention assures, with the help of the patient, that all treatment charges are captured and that treatment is properly terminated.

As discussed above, the system of the invention can be used, inter alia, for patient identification to ensure that the correct patient is being treated and the correct treatment is being given, as well as for controlling access to a commercial radiation treatment machine unit, such as the LANTIS® machine, which has its own record and verify (R&V) monitor. In accordance with a further aspect of the invention, provision is made for the use of particular timeouts (counted down time periods or timeouts) incorporated into the treatment procedure (including, or exclusively, the setup portion of the procedure prior to actual treatment) so as to ensure that the treatment sequence is being properly followed and/or to control access to the R&V monitor of the radiation treatment unit or, more generally, any medical treatment unit used in the procedure.

This aspect of the invention will be described in connection with FIG. 4, although it is to be understood that this specific embodiment is merely exemplary. As indicated in the first column of the flowchart shown in FIG. 4, in the specific embodiment illustrated, after start (block 110), two separate timeouts of, in this embodiment, 30 seconds each, are provided as indicated by blocks 112 and 116, to ensure that a treatment therapist and verification therapist each swipes his or her badges (decision diamonds 114 and 118). Further, a patient photograph must be scanned (block 120) a dialog box displayed (block 112) so as to enable the therapist to confirm that the correct patient is being treated.

As is also shown in FIG. 4, if these things are done and either an "OK button" is pressed or a further 30 seconds elapses (block 124), the R&V monitor (or other treatment unit) is enabled, if present (block 126).

In the next step, a "TIMEOUT #1" period of, in this example, 20 minutes, is then started (block 128) and if, during this period (block 130) the patient photograph is scanned (decision diamond 132), an audio signal which uniquely identifies the patient and which is described above, is generated (block 134). This audio signal is referred to in FIG. 4 as the patient's SOUNDTREAT™. Thereafter, a patient check sheet corresponding to that described above is scanned (block 136) and the same audio signal (i.e., SOUNDTREAT™) is again generated (block 140). As shown, if these things are done within the timeout period (20 minutes in this specific embodiment), the process proceeds to the next (third) column. If not, the sequence goes to ①(the last column), and the R&V monitor is disabled. Thus, the radiation treatment machine is "taken away" from the therapists if the required scans of the patient photograph and the patient check sheet are not made.

As is further shown in FIG. 4, if the two audio signals discussed above are generated as required, a "TIMEOUT #2" period (block 142) is begun which, in this specific embodiment, lasts two (2) minutes. This period is chosen as being a time period sufficient for the radiation treatment to be carried out. As indicated, a therapist can wait for the period to end (block 144) or can end the treatment session early by pressing an "end session" button (block 146). If the end session button is pressed, the sequence goes to ① decision diamond 146) and the R&V monitor is disabled (block 160). Similarly, if the timeout period elapses, the R&V monitor is also disabled (block 148).

Although it is contemplated that the treatment session would be completed within the time period provided, in order to cover a situation wherein, for some reason, the treatment has not been completed, an "Are You Still Treating?" dialog box (block 150) is displayed on the monitor screen and a "TIMEOUT #3" countdown (of, in this case, 60 minutes) is begun, as indicated by block 152. If "YES" is the response from the therapist, the R&V monitor is enabled (block 158) and the sequence begins again at "TIMEOUT #2." If "NO," the sequence goes to ① and the R&V monitor is disabled (block 160).

The rest of the ① sequence (last column) after block 160 provides for the display of the dialog box "Document Treatment—Full, Partial or None" (block 162) and after the system waits for the therapist selection (block 164), display of the dialog box 166 "Confirm Check Sheet Was Updated" to make certain that these things are done. This display persists indefinitely. In this specific embodiment, the last step may be omitted if desired. The system waits for the period to expire or therapist input (block 154), and as indicated by decision diamond 156, upon completion of the sequence the system returns to the start of the sequence (block 168).

Although the discussion above in connection with FIG. 4 is in the context of radiation treatment and, in the specific example given, relates to controlling access to the record and verify monitor of a radiation treatment machine or unit, it will, of course, be appreciated that the basic approach has broader application. For example, although the use of a patient specific audio signal (the SOUNDTREAT™ referred to above) is highly advantageous, a more conventional patient identification process, such as the swiping of a card and the consequence display of the patient's name for cross checking, can be used as part of the "time out" processing instead of the generation of an audio signal.

A key aspect of the basic method concerns the timing out of a specified predetermined time period so that it can be ensured that certain prescribed acts or actions are carried out within this period. This method can be applied to a number of hospital and other medical settings and, just as one example, can be used in the dispensing of drugs or other medications. In this example, when, e.g., a syringe containing a particular drug is delivered for use, and the drug and dosage are displayed on a screen of a control monitor (computer) by, e.g., scanning an identifier such as a bar code on the syringe, the method and system would provide for blanking out of the screen, or some other interruption of the delivery function, if one or more prescribed acts or actions are not performed within a predetermined period. As an example, such interruption would occur if a patient identifier (e.g., an identification card or bracelet which matches the drug requisition code for the patient) is not scanned within a predetermined short time period as timed out by the system. Alternatively, or in addition, the system would time out a further period during which the drug must be administered. This ensures that the drug and patient are properly matched up and that once matched, the drug is promptly administered.

The reason that the features discussed above in connection with the administration of drugs are important is that there can be problems with the general drug delivery process where, for example, a number of different drugs are delivered at the same time (or during closely spaced time periods) for administering to different patients. Moreover, the second aspect or feature discussed above, i.e., timing out the period during which the drug must be administered, addresses the situation where the drugs and patients are initially properly matched by the computer, and thus are shown as being properly linked together in the computer records, but where there is a substantial delay in administering the drug (e.g., where the therapist is called away to perform a different task), the drug is not removed from the delivery point for delivery to the patient, and thereafter a different drug at the delivery point is mistakenly picked up and delivered to the patient to be administered by the treating practitioner. Unfortunately, such an error would not be subsequently detected from the computer records because the computer records would show a proper matching of drug to patient. However, by encouraging the treating practitioner to carry out the drug administration promptly, this kind of error can be largely avoided.

In one preferred implementation, the basic system, i.e., a computer and display (e.g., a CPU and monitor) and a suitable identifier device (e.g., a card swipe), would be part of a mobile unit which would be moved to different stations or different machines. The mobile unit would be used, for example, to enable access to a particular machine only after one or more tasks, which would be monitored by the unit by virtue of, e.g., swiping of a corresponding identifier card, are carried out within a predetermined time period.

In accordance with a further aspect of the invention, an informational message is displayed on the associated monitor or other display as part of the treatment and/or the patient processing procedure and in particular, in connection with the ICD-9 evaluations mentioned above. In this regard, specific diagnosis codes are currently provided in connection with ICD-9 evaluations (e.g., 185 for prostate cancer) and the current system matches the code with a treatment code (CPT) and in some instances, may "kick out" a treatment or otherwise provide an alert that the treatment may be inappropriate. In accordance with this aspect of the invention, an educational display is provided based on the ICD-9 code so that a suitable message is presented on the monitor which is tailored to the particular disease being treated. Further, the system would track the number of treatments that have been given and provide a different message where the number of treatments warrant this. The display would thus be based on the condition of the patient and the ICD-9 code and, of course, no specific patient information, i.e., information identifying a particular patient, would be provided.

In a preferred embodiment, the messages would provide information about the particular disease (e.g., the specific cancer) being treated including recommended drugs to be taken at the end of the treatments. As indicated above, the display would be based on the ICD-9 code, the potential side effects and/or the number of treatments, and could be provided every day, with the option to select a further message. Particularly where a specific drug was being recommended and/or discussed, an arrangement could be made for the messages to be sponsored by the corresponding drug manufacturer.

In one implementation, the message display would be related to the time out procedures discussed above, and the system would provide that the display would be presented at certain specific times, such as the end of a particular treatment, e.g., when the "Document Treatment-Full, Partial or None" dialog box was displayed. In this regard, the therapists, being caregivers, would normally like to provide such a message to a patient as a positive part of the treatment and thus the therapists would be given an incentive to complete the patient treatment and close out the treatment process so that the patient will receive the message. This close out procedure is, of course, essential, but completion is sometimes delayed. With the present invention, as stated above, the therapist would normally be motivated to ensure that this small reward, in the form of providing a positive informational message, would be presented to his or her patient and thus would be motivated to close out the treatment procedure to thus ensure that the message is automatically presented.

More generally, apart from the timed procedures described above, there are other advantages associated with the presentation of a dialog box or the like wherein the therapist or other caregiver provides a simple, limited response, e.g., a simple touching of a touch-type computer screen, as to whether full, partial or no treatment is given. This simple input can be critical in certain situations. For example, in a radiation therapy setting, an indication that only partial treatment has been given can be a "red flag" indicating that something is wrong in a situation where a full treatment was prescribed. It is noted that, in general, with current procedures there is no convenient way for a caregiver to note that only a partial treatment was given and thus, such partial treatments often goes unreported. By enabling rapid documentation by simply touching a screen, reporting of a partial treatment is strongly encouraged. This is, of course, also very helpful in making certain that treatments are properly billed for, and, in particular, are not billed for when not performed. Again, this basic concept is applicable to areas of healthcare other than radiation therapy, including those discussed below, including a nursing home setting where, e.g., eating of a meal would also be reported as "full, partial or none."

In accordance with yet another feature of the "timeout" or "countdown" aspect of the invention, if the acts or tasks to be performed are not carried out within a predetermined time period (timeout period), the system presents certain queries to the user, e.g., by presenting corresponding dialog boxes on the computer or monitor screen. Again, considering a medical setting, one goal is to tie the various tasks together so that certain tasks, such as the scanning of a drug and the scanning of a patient's wristband, are performed with short time period. To ensure this, a further dialog box is presented after a time out which must be addressed before the therapist can move on to other tasks, and this thus helps assure that the things needed to be done are done within the required period.

Further, particularly with radiation treatments, it is desirable to wait until the end of the relatively long period (e.g., 20 minutes) for set up before generating the patient's audio signal (SOUNDTREAT™), i.e., to do this just prior to treatment. The relatively long time period ensures that the machine is properly set and the patient is properly set up on the treatment table prior to treatment. This relatively long period is provided after, e.g., the photograph identifier is scanned to enable access to the radiation equipment. Thus, if the requisite patient identifier used for generating the patient specific audio signal (SOUNDTREAT™) is scanned to quickly, i.e., too early in the pre-treatment period, the system will override the long (e.g., 20 minute) period and reset or cut down the period for using the radiation machine to the relatively short audio signal period (e.g., about 2 minutes). This means that if the treatment is not carried out within the short period, the radiation machine will be taken away from the therapist and an "Are You Still Treating?"

prompt corresponding to that described above will be generated. As in the system previously described in connection with FIG. 4, the therapist must then press "YES" to obtain an additional short period of time (e.g., an additional 2 minutes). This approach thus encourages the therapist to have everything fully set up for treatment prior to swiping the identifier that produces the patient specific audio signal and beginning the treatment.

As indicated above and will be evident, basic concepts associated with the checking methods described above have wider application than radiation therapy and can generally be applied to other healthcare settings. For example, the same basic approach can be taken in the administration of healthcare in general, i.e., administration of a specific patient care intervention or activity by a caregiver, such as the administration of drugs. In accordance with an important implementation of this basic approach, the following steps are carried out: (i) the parameters associated with the patient care intervention (e.g., drug treatment) are entered into a control monitor (computer and monitor), whether automatically (e.g., from a previously stored drug prescription) or by a medical practitioner from a patient treatment chart (e.g., a chart or record containing the prescription), (ii) the entries are verified against at least one source (e.g., a paper record or chart, in consultation with another caregiver or medical practitioner, or even based on the knowledge of the caregiver), (iii) selected critical parameters are entered into a paper verification sheet or check sheet, (iv) the healthcare intervention is carried out (e.g., the drug is administered), and (v) the patient record is updated. In this setting, the latter step may simply consist of making an entry into the computer monitor that intervention has been carried out (e.g., the drug has been administered). As a final step (vi), the check sheet or paper verification sheet is signed off. This can be done after the intervention or treatment (in this case, the administering of the drug) is given but preferably before the computer is told by an appropriate entry that the treatment has been given.

As indicated above in connection with the radiation therapy embodiment, the use of a check sheet wherein only three treatment parameters are to be entered is a very important feature. It has been found that keeping of a default paper log (record) is a key aspect of effective cross checking in connection with radiation therapy but that the entry of data into a check sheet may be resisted by the caregiver if more than three entries are required. Thus, by limiting the entries to the three that are most critical for the particular treatment or healthcare task, the burden on the person making the entries is minimal and a very useful paper record will be generated. This paper record log can be used, for example, as a chronology of key events or interventions which are documented in greater detail in the electronic medical record or in the patient's medical record.

More generally, the check sheet as used with the administration of healthcare, also referred to herein as a patient care intervention, would be limited to no more than three parameters exclusive of parameters relating to the time of the administration of the healthcare (intervention), i.e., the date, the time of day or both. In the latter regard, at least the date will be provided on any check sheet as a matter of course. In an example of a check sheet to be used in connection with the administration of drugs, a corresponding check sheet would be provided which would be limited to three parameters consisting of: (i) drug, the particular drug administered; (ii) dose, the particular dose given; and (iii) route, the route of administration (e.g., by i.v.). As indicated above, such a chart would generally provide the date and time as a matter of course and this would be filed in as well. Similarly, for a saline injection, the three parameters might be: (i) drug (i.v. bag) (normal saline or another identifier as appropriate); (ii) dose (e.g., "with 20 Meq K") and (iii) route (rate) (e.g., "80 cc per hr."). For another type of injection, the same headers could be used, e.g., drug (i.v. bag) (e.g., Furosemide), dose (e.g., 40 mg) and route (rate) (e.g., i.v. push). An example in radiology might be: (i) type (e.g., MRI), (ii) body part (e.g., brain) and (iii) contrast. Yet another example is discussed below in connection with nursing care wherein, for meals for the patient, the listing of the three parameters might be: (i) particular meal (e.g., dinner); (ii) meal eaten? and (iii) time of day. In this case, only two parameters in addition to the "time" parameter are listed.

It will, of course, be understood that these examples are merely illustrative and that while the parameters noted in these examples are believed to be beneficial or advantageous, the invention is not limited to these examples and a different combination of parameters might be preferred in some circumstances. Further, as stated above, the approach can be extended to different treatments or medical or healthcare tasks, referred to herein as patient care interventions, other than those specifically discussed above.

It is also to be understood that the patient care intervention can be a simple one such as the elevation of the head of the patient's bed in response to the patient being short of breath. A log entry can be important here simply to provide a record of the fact that the intervention that was needed was, in fact, provided.

It should also be understood that the invention is not limited to the generation of, and signing off on, a single treatment check sheet or paper verification sheet. In some settings, two (or even more) check sheets may be appropriate. For example, the treatment check sheet may be what is referred to as short hand "nurse's notes," i.e., a sheet or chart containing short notes which are taken by the nurse during the procedure and which become part of the complete treatment record or medical record. The short log notes may be used by the caregiver as a basis for more detailed "end of shift" notes later. In a specific example, these nurse's notes would also be signed off by the caregiver in addition to a medication administration report (MAR).

In some situations, both a high level check sheet and a low level check sheet can be generated, with the first check sheet being the responsibility of a higher level medical practitioner and dealing with more complex parameters and the second dealing with more routine matters and being the responsibility of a hospital caregiver with more limited training and experience. For example, in the case of a nursing home (see the discussion below), a more highly trained and skilled professional might be in charge of medications and have a check sheet concerning the medications given to a patient (e.g., the "drug," "dose" and "route (rate)" list mentioned above) while a less skilled caregiver might be in charge of food service and have a corresponding check sheet (e.g., the "meal," "eaten?" and "time of day" list also mentioned above). In such a case, it would be helpful if the two types of check sheets were of different colors or otherwise readily identifiable one from the other.

Although the record and verification techniques discussed above have been described in connection with the use of a computer monitor, it will be understood that a computer monitor may not be available in all treatment settings and even in hospitals where computer monitors are available, situations arise where the intervention (e.g., the prescribed treatment or procedure) is not immediately entered into the computer monitor. In the latter regard, in an emergency situation, a doctor may simply call in the data regarding a drug to be administered and while this data may be entered into the computer later, it is important that the prescribed treatment be entered into a formal treatment log to provide a real time record. This log would include the patient's name, the date and time and spaces for entering the critical data. In a preferred embodiment, the log includes three columns for entry of critical parameters and another column or entry space for the date and time. The critical data would advantageously comprise data or parameters such as discussed above. In a beneficial implementation, all of the relevant information is put into the log, then into a computer and a space or box is provided on the treatment log to enable marking of the log (e.g., checking or initialing the space or box) if the computer entry is made. In addition, as part of the method, provision is preferably made for circling or otherwise marking an original entry if, for whatever reason, the treatment is not carried out after the entry is made.

As indicated previously, another medical or healthcare setting in which the basic system of the invention can be employed is a nursing home. In this application, an individual monitoring system, including a computer and monitor, and, preferably, an optical reader or badge swipe device, would be provided in each room. In use, the caregiver swipes his or her badge and, in a preferred embodiment, a characteristic tone or other audio signal assigned to the patient is generated as described above. In one advantageous embodiment, a patient chart with a patient identifier is also swiped as well, and a patient specific audio signal is generated if there is a match with a stored identifier. This assures the patient that he or she is being cared for by an authorized person and that the patient chart is the correct one, something that can be of real comfort to, e.g., patients who are infirm or essentially helpless.

In one implementation of this application, the action of the caregiver in swiping his or her badge (whether or not a patient specific audio signal is generated) activates a presentation of check sheet or check list which appears on the monitor screen. However, in another implementation, the check sheet would simply be carried into the room by the caregiver, as described above. The purpose of the check sheet in this instance is to monitor and control patient care intervention matters or issues such as turning of the patient in bed and patient food intake. It is important to understand the problem of patient neglect is a serious one in many nursing homes around the country and the simple act of turning the patient is important to prevent so-called "bed sores," i.e., pressure ulcers. Recent studies have demonstrated that the costs associated with pressure ulcers is staggering, particularly given the preventable nature of the problem in most situations. If a caregiver is required to check off an entry on a chart, preferably by making a designated computer monitor entry, that this duty has been performed, it is more likely that the turning of the patient will actually be carried out.

Oral intake is an important indicator of the well-being of a patient and can be monitored by, for example, the simple lifting of the lid on the food tray, observing whether the food or liquids served have been eaten or not, and reporting what is observed, e.g., by checking a box, either manually on a paper check sheet, or preferably, by making a designated monitor entry. The latter is preferably a simply entry made in response to a dialog box presented on the monitor screen (e.g., MEAL EATEN? YES/NO). Of course, the query and response could be more complex (e.g., partially eaten, not eaten, a particular food (e.g., dessert) eaten) but, in general, for a nursing home setting, in contrast to hospital setting, wherein the lowest level caregivers may have limited language and/or technical skills, a simple "yes/no" response may be preferred. In another embodiment, a paper check sheet may be used in place of or in addition to the monitor entry. As discussed elsewhere in this application, in an important implementation, the entries to be made in the check sheet would be limited to three critical items (generally corresponding to the treatment parameters discussed above), and, for example, could consist of (i) the particular meal (e.g., breakfast or dinner), (ii) whether the meal was eaten or not, and (iii) the time of day. In the latter regard, the time of day can be important in that, as will be appreciated, it sometimes occurs in a nursing home that, for various reasons, "dinner" is not eaten at what would normally be considered dinner time.

A further parameter that can be important to monitor in a nursing home is the pattern of interest shown to the patient by non-staff members, i.e., family, friends and others. Accordingly, an entry can be provided on the reporting sheet or check sheet for "family present" or "visitors present" and this can be monitored by the nursing home. In this regard, a patient who has a constant stream of visitors may not need the same amount of checking on by staff as one who has no visitors at all and this can be taken into account based on the daily report generated.

Referring to FIGS. 12 to 17, there is shown a preferred embodiment of a further aspect of the invention. This aspect of the invention refers to a document holder or carrier for medical documents, medical patient identifiers (identification cards, patient photographs, etc.) and the like. The carrier, which is generally denoted 170, is described below in connection with patient documents used in connection with radiation therapy but it will be understood that the carrier has broader application as will be indicated to some extent below.

Carrier or holder 170 includes a rectangular backing member 172, and a first rectangular transparent member 174 which is of slightly smaller dimensions than member 172 and which is heat sealed or otherwise affixed to backing 172 along two edges thereof so as to form a full pocket for receiving papers. Member 174 includes a gripping indentation 174a along one free edge thereof and the free edges may include a thin raised embossment or ridge (not shown) extending around the two free edges. The latter terminate inwardly of the corresponding edges of backing member 172, as shown. Carrier 170, as described thus far, corresponds to a prior art, commercially available product used as a folder for papers or the like, with the backing member 172 being made of an opaque plastic and the transparent cover sheet or member 174 being made of transparent plastic. In one embodiment of the carrier of the present invention described below, backing member 172 is made of a transparent plastic so as to permit viewing of the rearwardly facing surface of one of the documents contained therein.

Carrier 170 further includes a second transparent member 176 of a generally triangular shape affixed along two side edges thereof to member 174. As illustrated, member 176 may include, in the opposite side edge thereof, a gripping indentation 176a. Transparent member 176 preferably comprises a clear plastic sheet which is heat sealed or otherwise affixed to member 174 so that no seam is formed. Member 176 forms a partial pocket with member 174 which is easier to access than the full pocket formed by members 172 and 174 bur provides less secure holding of papers received therein. Although member 176 may be of other different shapes, in the preferred embodiment illustrated, the side edge sealed to, and extending along, the side edge of member 174 is at least 3 inches in height and preferably at least 7 inches in height so as to provide relatively secure retention of thin standard 8×11 paper documents, i.e., so as to prevent the paper documents from bending or flopping over as shown for document 177 in FIG. 17. A basic purpose of the partial pocket formed by members 174 and 176 is to provide temporary retention, i.e., transient storage, of a document (or documents) which is normally to be retained in the full pocket formed by members 172 and 174, as is explained in more detail below.

Figure 12:
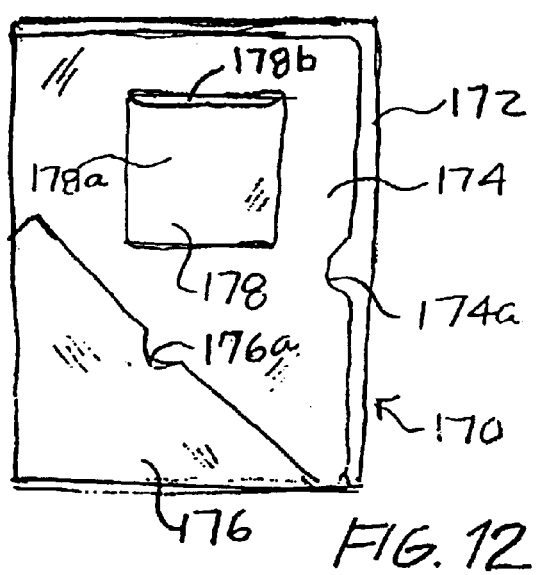
Figure 13:
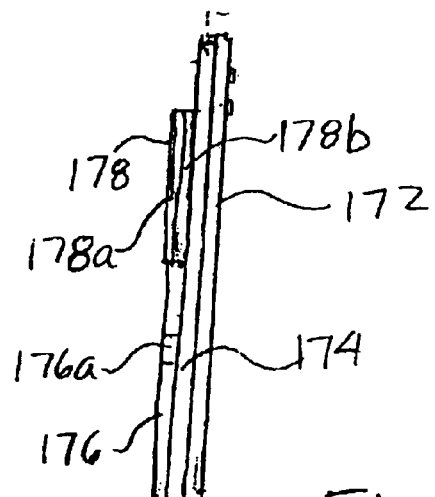
Figure 11:
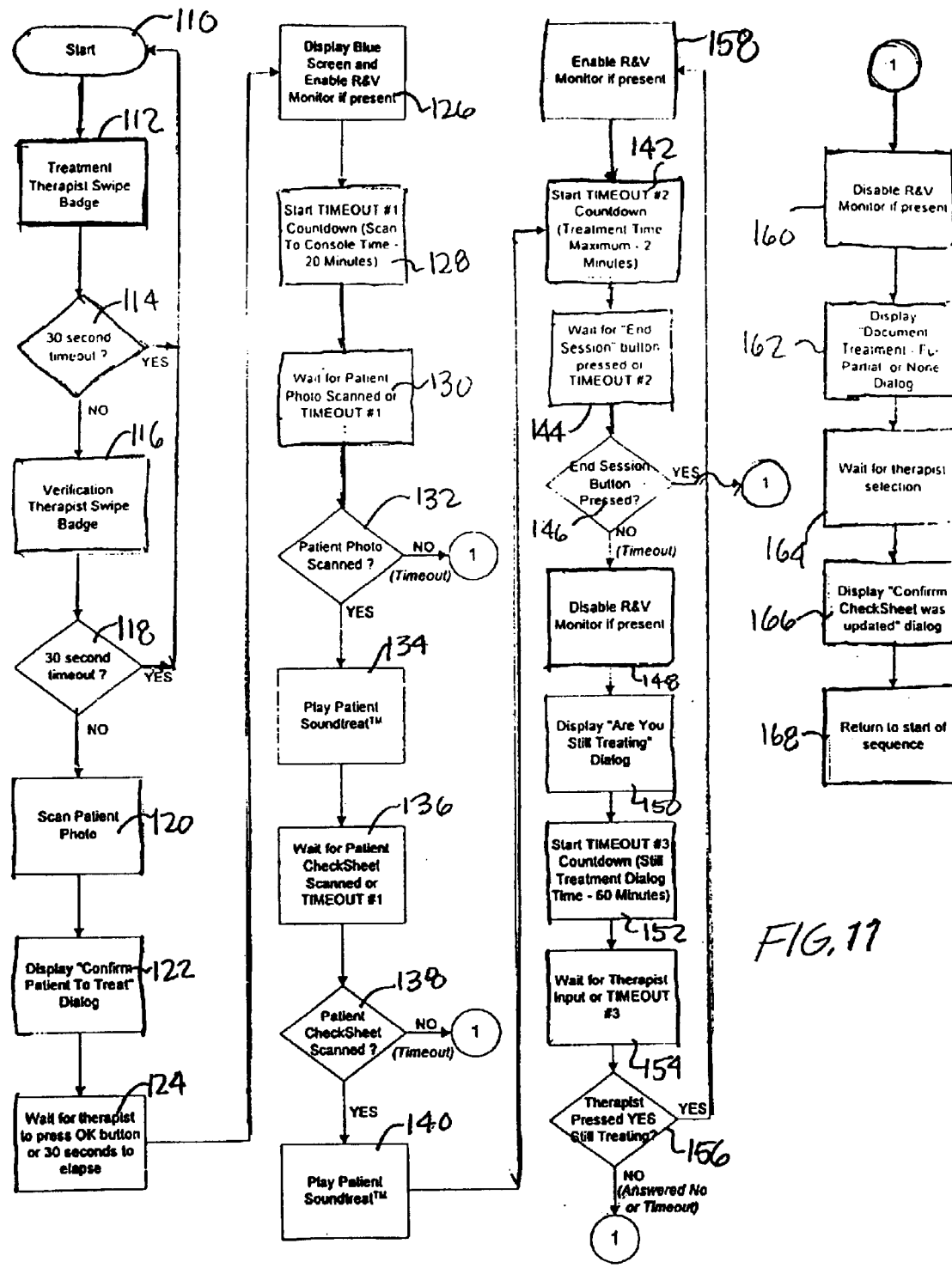
FIG. 11 is a flow chart of a record and verify method in accordance with yet another embodiment of the invention.

Carrier 170 further includes a transparent pocket or sleeve member 178 which is also affixed to second member 174 in different area thereof from that which member 176 overlays. As illustrated, pocket member 178 is preferably located near the top of carrier 170 centrally thereof. As is perhaps best seen in FIG. 13, pocket member 178 comprises front and back walls or sheets 178a and 178b which form a pocket therebetween. To this end, walls 178a and 178b are sealed together along the facing side and bottom edges thereof but not at the facing top edges so as to form a pocket configuration that opens at the top. The rear surface of back wall 178b of pocket member 178 is then affixed by suitable means to member 174. As shown in FIG. 12, pocket 178 is preferably formed such that front wall 178a is slightly shorter than rear wall 178b so as to enable better access to the pocket formed thereby.

As is perhaps shown in FIG. 14, carrier 170 further includes one or more fastener strips 180 of hooks and loops fasteners which are fixedly secured to the back surface of backing member 172 and which are adapted to be removably secured to corresponding fastener strips (not shown) provided at a suitable place at a treatment site or other location at which the documents carried by carrier 170 are to be used. For example, in radiation therapy applications, strips 180 would be used to removably mount carrier 170 on a wall near the accelerator or treatment couch so that the documents carried thereby would be readily accessible at the treatment site.

Figure 10:
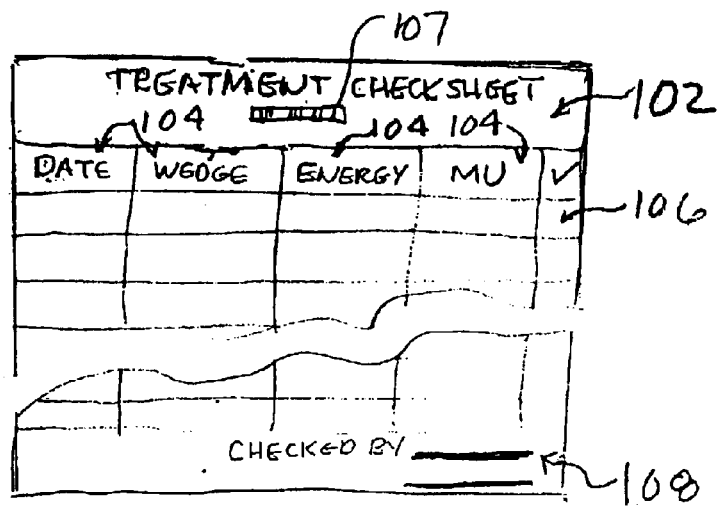
FIG. 10 is a schematic representation of a patient treatment check sheet in accordance with a further embodiment of the invention.

Before considering specific applications of carrier 170, conventional methods of providing documentation at the treatment side will be briefly considered. In many instances, the documentation for a particular patient is quite extensive and is contained in a bulky notebook. Because of this, the notebook is often not brought to the treatment site. Further, there is often no suitable place for the notebook to be put down and this can lead to the notebook being put down in unsuitable places (e.g., in an extreme case, in the wet sink area). Further, there are often frequent interruptions to the treatment process so that understandably the caregiver, when returning to the task at hand, momentarily forgets and thus must backtrack to determine where he or she is in the process and must refer to the large notebook or other compendium of documents. As indicated above, one underlying aim of the present invention is to ensure that the necessary documentation is present at the treatment site. In radiation therapy, for example, there are many, many documents generated and to avoid the need for all of these documents to be at hand at the treatment site, one aspect of the invention concerns compressing or stripping down of this documentation to only the necessary documents, as well as, in addition, providing stripped down treatment logs or treatment check sheets as described above in connection, for example, with FIG. 10. By reducing the documents to the necessary or critical documents and simplifying the documents themselves, the burden on the caregiver is substantially reduced and thus it is more likely that the needed documents actually will be brought to the treatment site. Further, by having the carrier 170 at the treatment site, as close to the patient as possible, the caregiver is encouraged to log critical time sensitive tasks in an efficient manner.

Turning to a specific example, and referring in particular to FIG. 14, carrier 170 is shown as carrying or holding a patient photograph 182 and two paper documents denoted 184 and 186. Photograph 182 is retained in member 178 and includes patient specific identifier (e.g., a patient specific bar code) 182a at the top thereof. Although the use of a photograph identifier is generally preferred because of the ready identification that can usually be made using the photograph, it will be appreciated that other patient identifier elements, such as an identification card, can also be used.

In a preferred implementation of this particular embodiment relating to radiation therapy, the documents 184 and 186 comprise, respectively, (i) a log sheet, e.g., in this application, a patient treatment chart, which is preferably of the type described above in connection with FIG. 10, and including a patient identifier (barcode) 184a, and (ii) a guide sheet, e.g., in this application, a sheet containing the set-up instructions for the patient and including, e.g., a diagram of a portion of the human body with the treatment area identified thereon. In an alternative embodiment, the guide sheet could, for example, include "nurse's notes," therapists' notes, and/or other special instructions about the care to be given to the particular patient. Similarly, the log sheet could be any of the various check sheets described previously. With these two essential documents, i.e., the guide sheet 184 and the log sheet 186, the treatment therapist has what he or she needs at the treatment site to carry out the radiation treatment or other medical care intervention and record the critical parameters used.

The barcodes 182a and 184a can be scanned through their plastic coverings and the entire carrier 170 can simply be swiped under or through the reader to provide scanning of barcodes 182a and 184a in sequence. The scanning process has been described above and, in this embodiment, the system would be programmed to require that the photograph 182 be scanned first and the log sheet 184 thereafter, as would be the case when the carrier 170 is passed or swiped through the reader or detector from the bottom. This ensures that the documents are in their proper place in the correct sequence in carrier 170.

After the initial scanning procedure, the guide sheet 186 may be taken out and put on top, either straight up, or turned on one side as shown in FIG. 16, so that the set up procedure can be carried out as set forth in document 186, by referring to document 186. Alternatively, as mentioned above, backing sheet 172 can also be made transparent and, in this embodiment, the guide sheet 186 can be oriented to face rearwardly and thus can be read through the back of carrier 170.

Because the photograph 182 and documents 184, 186 must be in place and in the proper sequence to enable successful scanning thereof, the caregiver is encouraged to put all of the documents back into carrier 170, and put them back in the proper order, for the next scanning operation. In one preferred embodiment, the document carrier 170 is also scanned at the end of a treatment or other intervention but the next scanning operation could simply be the next time that carrier 170 and the documents carried thereby are used.

Although the invention has been described above in relation to preferred embodiments thereof, it will be understood by those skilled in the art that variations and modifications can be effected in these preferred embodiments without departing from the scope and spirit of the invention.

What is claimed:

1. A record and verification method for use in monitoring healthcare administered to a patient, said method comprising the steps of:
   (a) initially entering, into a computer monitor, data corresponding to the healthcare to be administered;
   (b) verifying the patient healthcare data entered into the computer monitor against at least one source;
   (c) entering data from the computer monitor onto a paper verification sheet;
   (d) administering the healthcare to the patient; and
   (a) updating a patient record after the healthcare has been administered.

2. A method according to claim 1 wherein the step of updating a patient record comprises making an entry into the computer that the healthcare has been administered.

3. A method according to claim 1 further comprising checking and signing the paper verification sheet.

4. A method according to claim 3 wherein the step of updating a patient record comprises making an entry into the computer that the healthcare has been administered and the step of checking and verifying the paper verification sheet is carried out after said entry.

5. A method according to claim 1 wherein the data corresponding to the healthcare to be administered that is entered into the computer monitor is previously stored and is automatically downloaded into the computer monitor at the request of an operator.

6. A method according to claim 1 wherein the data corresponding to the healthcare to be administered is entered into the computer monitor from a patient healthcare administration chart.

7. A method according to claim 1 wherein said method is used with a radiation therapy treatment system including a radiation treatment device for providing radiation treatment and said computer monitor comprises a radiation treatment monitor and an associated computer for monitoring the radiation treatment device, wherein the healthcare data comprises radiation treatment data and said radiation treatment data is entered into the treatment monitor from a patient treatment chart, and wherein the step of administering healthcare comprises using the radiation treatment device in treatment of the patient.

8. A method according to claim 7 wherein only selected treatment data, of the patient treatment data that is entered into the treatment monitor, is entered onto the paper verification sheet.

9. A method according to claim 7 wherein multiple radiation fields are delivered to the patient, and steps (a) through (e) are repeated for each field, and the method further comprises entering of a cumulative radiation dose into the patient treatment chart when all of the multiple treatment fields have been delivered.

10. A method according to claim 7 wherein using the radiation treatment device generates actual treatment data, wherein the step of updating a patient record comprises entering said actual treatment data onto the patient treatment chart, and wherein said method comprises a further step of:
   (f) checking and signing the data entered into the patient treatment chart and into the paper verification sheet.

11. A method according to claim 10 wherein the selected treatment data consists of the (i) presence or absence of a wedge, (ii) the energy level used, and (iii) the monitor units used.

12. A method according to claim 10 wherein first and second radiation therapists carry out the method, and the first therapist is responsible for at least step (e), the second therapist is responsible for at least steps (b) and (c) and both therapists carry out, and are responsible for, step (f).

13. A method according to claim 12 wherein both the first and second therapists initially view, on a monitor screen associated with the treatment monitor, treatment data entered into the treatment monitor, the first therapist then recites aloud selected treatment data from the monitor screen, the second therapist, white still viewing the monitor screen, verifies the selected treatment data, in real time, as recited by the first therapist, the second therapist, while still viewing the monitor, recites aloud the preselected treatment data from the monitor screen, the first therapist, when still viewing the monitor screen, verifies the preselected treatment data, in real time, as recited by the second therapist, and the second therapist then enters the preselected treatment data into the paper verification sheet.

14. A method according to claim 12 wherein, after treatment data is entered into the treatment monitor and the data entered is displayed on a monitor screen associated with the treatment monitor, the first therapist recites aloud selected treatment data from the patient treatment chart and the second therapist verifies the recited treatment data against the data entered into treatment monitor as displayed on said monitor screen.

15. A method according to claim 14 wherein the second therapist verbally recites the treatment data displayed on said monitor screen.

16. A method for use in carrying out a medical treatment wherein a computer and a computer monitor including a monitor screen are used at least in setting up of the medical treatment, said method comprising:
   setting a time period in which at least one action requiring interfacing with the monitor must be carried out;
   monitoring whether the at least one action has been carried out during said time period; and
   if the at least one action is not carried out within said time period, at least temporarily providing that the medical treatment is not to proceed.

17. A method according to claim 16 wherein at least temporarily providing that the medical treatment is not to proceed comprises blanking out the monitoring screen.

18. A method according to claim 16 wherein at least temporarily providing that the medical treatment is not to proceed comprises providing a prompt on the monitor screen which requires a predetermined reply before the medical treatment is to proceed.

19. A method according to claim 16 wherein the at least one action comprises at least two separate actions, each with a separate time period for completion.

20. A method according to claim 16 wherein the at least one action comprises providing identification of one of (i) a patient to be treated and (ii) at least one treatment practitioner, and wherein said identification is provided by reading of an identifier by an optical reader associated with said control monitor.

21. A method according to claim 16 wherein said at least one action comprises scanning of an identifier by an optical reader associated with said computer monitor.

22. A method according to claim 21 wherein said identifier comprises a patient photograph.

23. A method according to claim 21 wherein said identifier is associated with identifying member for one of (i) a patient undergoing the medical procedure and (ii) at least one treatment practitioner.

24. A method according to claim 21 wherein said identifier is carried by a medical instrument.

25. A method according to claim 24 wherein the medical treatment comprises delivery of a drug and said medical instrument is a syringe.

26. A method according to claim 16 wherein at least temporarily providing that the medical treatment is not to proceed comprises providing that the at least one action must be carried out within a new time period before the medical treatment can proceed.

27. A method according to claim 26 wherein said at least one action comprises at least two actions both of which must be completed within said period.

28. A method according to claim 26 wherein the medical treatment includes the use of a treatment unit controlled by the computer and monitor and wherein at least temporarily providing that the medical treatment is not to proceed if the at least one action is not completed during said time period comprises prohibiting use of the treatment unit.

29. A method according to claim 28 wherein use of the treatment unit is prohibited by disabling the monitor.

30. A method according to claim 28 wherein the at least one action comprises (i) scanning of an identifier member, including a patient identifier, using an optical scanner associated with the computer monitor, and (ii) scanning of a patient treatment sheet, including said patient identifier, using said optical scanner, and wherein use of said treatment unit is prohibited if either said scanning is not carried out during said time period.

31. A method according to claim 30 wherein a characteristic audio signal, previously assigned to the patient undergoing the medical treatment and unique to the patient, is generated for each said scanning wherein the patient identifier matches an identifier for the patient stored by said computer.

32. A method according to claim 30 wherein the at least one action further comprises scanning of an identifier by at least one treatment practitioner within a predetermined time period prior to said scanning of the identifier member and the patient treatment sheet.

33. A method according to claim 30 wherein, when each said scanning is successfully completed, a further predetermined time period is started for use of said treatment unit, and wherein use of said treatment unit is prohibited at the end of said further period.

34. A method according to claim 33 wherein, after use of said unit is prohibited, said computer monitor displays a query on the monitor screen as to whether treatment is continuing and, in response to entry of a positive reply, enables the treatment unit.

35. A method according to claim 33 wherein when use of said unit is prohibited, said monitor displays on the monitor screen a query requesting confirmation that the patient treatment sheet has been updated.

36. A method for use in carrying out a medical procedure, using a treatment unit and a computer and monitor for controlling the treatment unit, so as to ensure that at least one action, requiring interfacing with the monitor, is completed in a timely manner, said method comprising:
   initiating at the monitor, a start time for the at least one action to be carried out;
   determining whether the at least one action has been carried out within a predetermined time period after said start time; and
   at least temporarily preventing access to the treatment unit if the at least one action has not been carried out within said predetermined period.

37. A check sheet for use in administration of patient healthcare, said check sheet containing (i) entry spaces for entry by a healthcare caregiver of healthcare parameters for verification, and (ii) headings for the entry spaces each identifying a corresponding healthcare parameter, said healthcare parameters consisting of no more than three parameters excluding parameters relating to the time of administration of the healthcare.

38. A check sheet according to claim 37 wherein the check sheet further include a heading for the time of day at which the patient healthcare is ad ministered.

39. A check sheet according to claim 37 wherein said check sheet comprises a treatment check sheet for a patient undergoing radiation treatments, said treatment check sheet listing a plurality of treatment parameters for entry of data for verification by at least one radiation treatment practitioner prior to administration of a radiation treatment, said treatment parameters consisting solely of three patient specific parameters.

40. A check sheet according to claim 39 wherein said three parameters consist of wedge presence, radiation energy level and monitor units.

41. A treatment check sheet as claimed in claim 39 wherein said treatment check sheet includes four rows or columns thereon, said rows or columns including headings and, following each of said headings, a plurality of empty spaces for entries by the treatment practitioner, said headings including wording indicating that the corresponding column is designated for entries with respect (i) the current date, (ii) the radiation energy level, (iii) the presence or absence of a wedge and (iv) monitor units.

42. A check sheet according to claim 41 wherein the treatment check sheet includes at least one place thereon designated for checking off by a treatment practitioner using the treatment check sheet.

43. A method of assisting in full completion of a medical procedure for an individual patient undergoing the medical procedure, said method comprising:
   assigning an audio signal to a patient and ensuring that the patient recognizes the assigned audio signal when said audio signal is generated;
   generating said audio signal at a treatment site during the medical procedure so that the signal is heard by the patient;
   providing for terminating of the audio signal only after treating personnel performs at least preselected action necessary to properly conclude the medical procedure; and
   instructing the patient to remain at the treatment site until the audio signal is terminated.

44. A method as claimed in claim 43 wherein the audio signal comprises a piece of music, wherein said piece of music is played while the patient is on a treatment table, and wherein the at least one action comprises updating of a treatment record for the patient.

45. A record and verification method for use with a radiation therapy system including a radiation treatment device for providing radiation treatment and a treatment monitor, including a computer, for monitoring the treatment provided by the radiation treatment device, said method comprising the steps of:
   (a) initially entering, into the treatment monitor, patient treatment data corresponding to that contained in a patient treatment chart;
   (b) verifying patient treatment data entered into the treatment monitor against at least one source;
   (c) entering treatment data from the treatment monitor onto a paper verification sheet;

(d) cross checking the treatment data entered onto said paper verification sheet;

(e) using the radiation treatment device in treating of the patient; and (f) updating the patient treatment chart after said treating of the patient.

46. A record and verification method in monitoring the administration of a patient care intervention, said method comprising the steps of:

(a) initially entering, into a computer including an associated monitor screen, data corresponding to the patient care intervention that is to be administered to a patient;

(b) accessing the computer by presenting to an optical detector associated with the computer an identifier corresponding to an identifier stored by the computer so that when there is a match between the presented identifier and the stored identifier, at least some of said entered data is displayed;

(c) administering a patient care intervention to the patient corresponding to the entered data displayed on the monitor screen;

(d) entering onto a paper verification sheet selected data related to the patient care intervention administered to the patient: and (e) making an entry into the computer that the patient care intervention has been administered.

47. A record and verification method for use in monitoring a medical treatment administered to a patient, said method comprising the steps of (a) initially entering patient treatment data corresponding to that contained in a patient treatment chart into a computer including an associated monitor screen;

(b) verifying patient treatment data entered into the computer and appearing on the monitor screen against at least one source;

(c) entering selected treatment data from that appearing on the monitor screen of the treatment monitor onto a paper verification sheet;

(d) cross checking the treatment data entered into the paper verification sheet;

(a) carrying out the treatment; and (f) entering into the patient treatment chart (i) an indication that the treatment has been carried out and (ii) an indication of any differences between the treatment data entered into the paper verification sheet and any actual treatment data.

48. A method according to claim 47 wherein said computer includes an associated optical detector and wherein access to said computer is effected by presenting to the optical detector an identifier member carrying an identifier matching an identifier stored by the computer.

49. A record and verification method for monitoring a patient care intervention administered to a patient, said method comprising the steps of:

entering critical data received relating to a patient care intervention, along with the name of the patient and the time and date, into a pre-prepared paper tog sheet;

verifying the critical data entered with at least one source;

carrying out the patient care intervention;

entering data relating to the patient care intervention into a computer monitor; and checking off on the paper log sheet that the data has been entered into the computer monitor.

50. A method according to claim 49 wherein, if the patient care intervention is not carried out or is riot fully carried out, the method further comprises marking the log sheet to indicate if the patient care is not carried out or is not fully carried out.

51. A monitoring method for monitoring a caregiver intervention, said method comprising:

providing an electronic presentation of an inquiry as to whether a particular patient intervention administered by a caregiver is best characterized as full, partial or none;

prompting the caregiver to provide a simple response to the inquiry; and recording the response of the caregiver to the inquiry for future use.

52. A method according to claim 51 wherein the inquiry is presented in a dialog box on touch sensitive computer screen and the caregiver responds by touching an appropriate screen location.

53. A method of verification of an identity of a patient to be treated, said method comprising:

scanning a patient identifier which identifies the patient to be treated and which is carried by a first item associated with treating of the patient;

scanning a further said patient identifier which is carried by at least one further item associated with treating of the patient; and generating a characteristic audio signal only if, after scanning of both said patient identifier carried by said first item and said further said patient identifier carried by said at least one further item, there is a match between each patient identifier scanned and a stored identifier.

54. A method according to claim 53 wherein said characteristic audio signal is generated only when said patient identifiers are scanned in a predetermined sequence.

55. A method according to claim 53 wherein one of said items associated with treating of the patient comprises a patient wristband and a further one of said items comprises a patient chart.

56. A method according to claim 53 wherein one of said items comprises a patient wristband and a further one of said items comprises a medication container for medication for the patient.

57. A method for verification that necessary actions have been taken in connection with a treatment of a patient at a treatment site, said method comprising:

scanning a patient identifier which identifies the patient to be treated and which is carried by a first item associated with one action in treating of the patient;

scanning at least one further patient identifier which is carried by at least one further item carried by a second item associated with a further action in treating of the patient;

determining whether there is match between the scanned patient identifier and a stored identifier in response to scanning of both said first patient identifier and said at least one further patient identifier; and generating a characteristic audio signal only if a match is indicated for both said first and said at least one further identifier so as to thereby indicate that said one action and said further action have taken place.

58. A method according to claim 57 wherein said first and further items are associated with actions that each must take place to complete a treatment task in connection with treatment of the patient.

59. A method according to claim 58 wherein said task comprises bringing the treatment site each of a plurality of items which are to be used in said treatment.

60. A method according to claim 57 wherein said characteristic audio signal is generated only when said patient identifiers are scanned in a predetermined sequence.

61. A method according to claim 57 wherein said first item associated with treating of the patient comprises a patient wristband and said one action is ensuring that the patient has said wristband and said at least further item comprises a patient chart and said at least one further action is ensuring that the patient chart is present at the treatment.

62. A method according to claim 57 wherein said one item comprises a patient chart and said further item comprises a medical instrument for use in treatment for the patient and wherein generation of said characteristic audio signal indicates that the patient chart and medical instrument are present at the treatment site.

63. A method of verification of an identity of a patient to be treated, said method comprising:

scanning a machine-readable patient identifier which identifies the patient to be treated and which is carried by a first item associated with treating of the patient;

scanning a further said machine-readable patient identifier which is carried by at least one further item associated with treating of the patient; and permitting carrying out of an action associated with treating of the patient only if, after scanning of both said patient identifier carried by said first item and said further said patient identifier carried by said at least one further item in a predetermined sequence, there is a match between each patient identifier scanned and a stored identifier.

64. A method according to claim 63 wherein the patient identifier carried by the first item further includes a first human readable identification symbol and the patient identifier carried by the second item includes a second human readable identification symbol different from the first human readable identification symbol.

* * * * *